US009668479B2

(12) United States Patent
Abel-Santos

(10) Patent No.: US 9,668,479 B2

(45) Date of Patent: Jun. 6, 2017

(54) **MODULATING GERMINATION OF *PAENIBACILLUS LARVAE***

(71) Applicant: THE BOARD OF REGENTS OF THE NEVADA SYSTEM OF HIGHER EDUCATION ON BEHALF OF THE UNIVERSITY, Las Vegas, NV (US)

(72) Inventor: Ernesto Abel-Santos, Las Vegas, NV (US)

(73) Assignee: The Board of Regents of the Nevada System of Higher Education on Behalf of the University of Nevada, Las Vegas, Las Vegas, NV (US)

(*) Notice: Subject to any disclaimer, the term of this patent is extended or adjusted under 35 U.S.C. 154(b) by 0 days.

(21) Appl. No.: 14/578,091

(22) Filed: Dec. 19, 2014

(65) Prior Publication Data

US 2015/0173357 A1 Jun. 25, 2015

Related U.S. Application Data

(60) Provisional application No. 61/919,224, filed on Dec. 20, 2013.

(51) Int. Cl.

| | |
|---|---|
| ***A01N 43/38*** | (2006.01) |
| ***A61K 31/40*** | (2006.01) |
| ***A01N 31/08*** | (2006.01) |

(52) U.S. Cl.

CPC ............ *A01N 43/38* (2013.01); *A01N 31/08* (2013.01)

(58) Field of Classification Search

None

See application file for complete search history.

(56) References Cited

PUBLICATIONS

Faria et al. (World J Microbiol Biotechnol, 29, 217-221; published online Sep. 27, 2012).*

Burger's Medicinal Chemistry and Drug Discovery, Fifth Edition, vol. I: Principles and Practice, Wiley-Interscience 1995, pp. 783-802, 784.*

Abel-Santos and Dodatko, "Differential nucleoside recognition during Bacillus cereus 569 (ATCC 10876) spore germination," New J. Chem., 31:748-755 (2007).

Akoachere et al., "Identification of an in vivo inhibitor of Bacillus anthracis sterne spore germination," J. Biol. Chem., 282:12112-12118 (2007).

Alippi et al., "Evidence for plasmid mediated tetracycline resistance in Paenibacillus larvae, the causal agent of American Foulbrood (AFB) disease in honeybees," Vet. Microbiol., 125:290-303 (2007).

Allipi, "Detection of Bacillus larvae spores in Argentinian honeys by using a semi selective medium," Microbiol. Semin., 11:343-350 (1995).

Alvarez and Abel-Santos, "Potential use of inhibitors of bacteria spore germination in the prophylactic treatment of anthrax and Clostridium difficile-associated disease," Expert Rev. Anti. Infe., 5:783-792 (2007).

Alvarez et al., "Testing nucleoside analogues as inhibitors of Bacillus anthracis spore germination in vitro and in macrophage cell culture," Antimicrob. Agents Chemother., 54:5329-5336 (2010).

Bailey and Lee, "Bacillus larvae: Its cultivation in vitro 411 and its growth in vivo," J. Gen. Microbiol., 29:711-717 (1962).

Barlass et al., "Germination of Bacillus cereus spores in response to L-alanine and to inosine: The roles of gerL and gerQ operons," Microbiol., 148:2089-2095 (2002).

Berge et al., "Pharmaceutical Salts," J. Pharm. Sci., 66:1-19 (1977).

Bergey et al., 2009. Bergey's Manual of Systematic Bacteriology. Williams & Wilkins, New York.

Bertolini et al., "A new rational hypothesis for the pharmacophore of the active metabolite of leflunomide, a potent immunosuppressive drug," J. Med. Chem., 40:2011-2016 (1997).

Broodsgaard et al., "Response of in vitro reared honey bee larvae to various doses of Paenibacillus larvae larvae spores," Apidologie, 29:569-578 (1998).

Broussolle et al., "Diversity of spore germination in response to inosine and L-alanine and its interaction with NaCl and pH in the Bacillus cereus group," J. Appl. Microbiol., 105:1081-1090 (2008).

Colibar et al., "The effect of acidifiant on the development of bee families (*Apis mellifica*)," Lucrari Stiintifice—Universitatea de Stiinte Agricole a Banatului Timisoara, Medicina Veterinara 43:296-299 (2010).

Cortezzo et al., "Analysis of the action of compounds that inhibit the germination of spores of *Bacillus* species," J. Appl. Microbiol., 96:725-741 (2004).

Crailsheim and Riessberger-Galle, "Honey bee age-dependent resistance against American Foulbrood," Apidologie, 32:91-103 (2001).

Crailsheim, "Transport of leucine in the alimentary canal of the honeybee (*Apis mellifera* L.) and its dependence on season," J. Insect Physiol., 34:1093-1100 (1988).

Davidson, "Ultrastructure of American Foulbrood disease pathogenesis in larvae of the worker honey bee," *Apis mellifera*. J. Invertebr. Pathol., 21:53-61 (1973).

Dingman and Stahly, "Medium promoting sporulation of Bacillus larvae and metabolism of medium components," Appl. Environ. Microbiol., 46:860-869 (1983).

Dobbelaere et al., "Disinfection of wooden structures contaminated with *Paenibacillus larvae* subsp *larvae* spores," J. Appl. Microbiol., 91:212-216 (2001).

Dodatko et al., "Bacillus cereus spores release alanine that synergizes with inosine to promote germination," PloS One, 4:e6398, 8 pages (2009).

Dodatko et al., "Dissecting interactions between nucleosides and germination receptors in Bacillus cereus 569 spores," Microbiol., 156:1244-1255 (2010).

(Continued)

*Primary Examiner* — Dennis Heyer
*Assistant Examiner* — Daniel M Podgorski
(74) *Attorney, Agent, or Firm* — Ballard Spahr LLP

(57) ABSTRACT

Materials and methods for stimulating or inhibiting germination of *Paenibacillus larvae* spores, including methods for inhibiting *P. larvae* germination to reduce foulbrood in honey bees.

16 Claims, 12 Drawing Sheets

(56) References Cited

PUBLICATIONS

Eischen and Graham, "American Foulbrood survey in honey bees pollinating California almonds II: A disease equivalent number of spores," Am. Bee. J., 145:390-391 (2005).
Fey et al. "Identification of D-alanine as the auto-inhibitor of germination of Bacillus globigii spores," J. Gen. Microbiol., 35:229-236 (1964).
Foerster and Foster, "Response of Bacillus spores to combinations of germinative compounds," J. Bacteriol., 91:1168-1177 (1966).
Fries and Camazine, "Implications of horizontal and vertical pathogen transmission for honey bee epidemiology," Apidologie, 32:199-214 (2001).
Fries et al., "Vertical transmission of American Foulbrood (*Paenibacillus larvae*) in honey bees (*Apis mellifera*)," Vet. Microbiol., 114:269-274 (2006).
Genersch et al., "Strain- and genotype-specific differences in virulence of *Paenibacillus larvae* subsp *larvae*, a bacterial pathogen causing American Foulbrood disease in honeybees," Appl. Environ. Microbiol., 71:7551-7555 (2005).
Genersch et al., "Reclassification of *Paenibacillus larvae* subsp. *pulvifaciens* and *Paenibacillus larvae* subsp. *larvae* as *Paenibacillus larvae* without subspecies differentiation," Int. J. Syst. Evol. Microbiol., 56:501-511 (2006).
Genersch, "American Foulbrood in honeybees and its causative agent, Paenibacillus larvae," J. Invertebr. Pathol., 103:S10-S19 (2010).
Gillard et al., "Distribution of Paenibacillus larvae spores inside honey bee colonies and its relevance for diagnosis," J. Invertebr. Pathol., 99:92-95 (2008).
Guidi-Rontani et al., "Germination of Bacillus anthracis spores within alveolar macrophages," Mol. Microbiol., 31:9-17 (1999).
Guidi-Rontani et al., "Identification and characterization of a germination operon on the virulence plasmid pXO1 of Bacillus anthracis," Mol. Microbiol., 33:407-414 (2002).
Hills, "Chemical factors in the germination of spore-bearing aerobes. The effects of amino-acids on the germination of Bacillus anthracis, with some observations on the relation of optical form to biological activity," Biochem. J., 45:363-370 (1949).
Hirakawa et al., "Secreted indole serves as a signal for expression of type III secretion system translocators in enterohaemorrhagic *Escherichia coli* O157: H7," Microbiol., 155:541-550 (2009).
Hornitzky and Nicholls, "J medium is superior to sheep blood agar and brain heart infusion agar for the isolation of Bacillus larvae from honey samples," J. Apic. Res., 31:51-52 (1993).
Hornstra et al., "Characterization of germination receptors of Bacillus cereus ATCC 14579," Appl. Environ. Microbiol., 72:44-53 (2006).
Howerton et al., "Mapping interactions between germinants and Clostridium difficile spores," J. Bacteriol., 193:274-282 (2011).
Huo et al., "Investigation of factors influencing spore germination of Paenibacillus polymyxa ACCC10252 and SQR-21," Appl. Microbiol. Biotechnol., 87:527-536 (2010).
Johnson et al., "Influence of temperature on germination and growth of spores of emetic and diarrheal strains of Bacillus cereus in a broth medium and in rice," J. Food Sci., 48:286-287 (1983).
Jood and Kapoor, "Protein and uric acid contents of cereal grains as affected by insect infestation," Food Chem., 46:143-146 (1993).
Karakaya et al., "Antioxidant activity of some foods containing phenolic compounds," Int. J. Food Sci. Nutr., 52:501-508 (2001).
Kim et al., "Indole and 3-indolylacetonitrile 523 inhibit spore maturation in Paenibacillus alvei," BMC Microbiol., 11:119-128 (2011).
Lee and Lee, "Indole as an intercellular signal in microbial communities," FEMS Microbiol. Rev., 34:426-444 (2010).
Lee et al., "Indole is an inter-species biofilm signal mediated by SdiA," BMC Microbiol., 7:42 (2007).
Lee et al., "Indole and 7-hydroxyindole diminish Pseudomonas aeruginosa virulence." Microbiol., 2:75-90 (2009).
Liming et al., "Fast determination of 26 amino acids and their content changes in royal jelly during storage using ultra-performance liquid chromatography," J. Food Compost. Anal., 22:242-249 (2009).
Lindstrom et al., "The distribution of Paenibacillus larvae spores in adult bees and honey and larval mortality, following the addition of American Foulbrood diseased brood or spore-contaminated honey in honey bee (*Apis mellifera*) colonies," J. Invertebr. Pathol., 99:82-86 (2008).
Lodesani and Costa, "Limits of chemotherapy in beekeeping: Development of resistance and the problem of residues," Bee World, 86:102-109 (2005).
Luu et al., "Cooperativity and interference of germination pathways in Bacillus anthracis spores," J. Bacteriol., 193:4192-4198 (2011).
McSpadden Gardener, "Overview of the nature and application of biocontrol microbes: *Bacillus* spp," Phytopathol., 94:1244-1244 (2004).
Nikaido et al., "AcrAB multidrug efflux pump regulation in *Salmonella enterica* serovar Typhimurium by RamA in response to environmental signals," J. Biol. Chem., 283:24245-24253 (2008).
Nordstrom and Fries, "A comparison of media and cultural conditions for identification of Bacillus larvae in honey," J. Apic. Res., 34:97-103 (1995).
O'Connor and Halvorson, "L-alanine dehydrogenase: A mechanism controlling the specificity of amino acid-induced germination of Bacillus cereus spores," J. Bacteriol., 82:706-713 (1961).
Paredes-Sabja et al., "Germination of spores of *Bacillales* and *Clostridiales* species: Mechanisms and proteins involved," Trends Microbiol., 19:85-94 (2011).
Peng et al., "Effects 467 of chlortetracycline of honey bee worker larvae reared in vitro," J. Invertebr. Pathol., 60:127-133 (1992).
Piccini et al., "Detection of *Paenibacillus larvae* subspecies *larvae* spores in naturally infected bee larvae and artificially contaminated honey by PCR," World J. Microb. Biot., 18:761-765 (2002).
Powell, "Factors affecting the germination of thick suspensions of Bacillus subtilis spores in L-alanine solution," J. Gen. Microbiol., 4:330-338 (1950).
Radwanski and Last, "Tryptophan biosynthesis and metabolism: Biochemical and molecular genetics," Plant Cell, 7:921-934 (1995).
Ramirez and Abel-Santos, "Requirements for germination of Clostridium sordellii spores in vitro," J. Bacteriol., 192:418-425 (2010).
Rembold and Dietz, "Biologically active substances in royal jelly," Vitam. Horm., 23:359-382 (1966).
Rodbard et al., "Statistical characterization of the random errors in the radioimmunoassay dose response variable," Clin. Chem., 22:350-358 (1976).
Romick and Tharrington, "An automated method for quantifying the L-alanine trigger of Bacillus subtilis spore germination and competitive inhibition by D-alanine," J. Rapid Meth. Aut. Mic., 5:215-221 (1997).
Ross and Abel-Santos, "The Ger receptor family from sporulating bacteria," Curr. Issues Mol. Biol., 12:147-158 (2010).
Salas and Ellar, "Uric acid and allantoin uptake by Bacillus fastidiosus spores," Febs. Lett., 183:256-259 (1985).
Sanz et al., "Detection of Bacillus anthracis spore germination in vivo by bioluminescence imaging," Infect. Immun., 76:1036-1047 (2008).
Schaeffer and Fulton, "A simplified method of staining endospores," Science, 77:194-194 (1933).
Sebaugh, "Guidelines for accurate EC50/IC50 estimation," Pharm. Stat., 10:128-134 (2011).
Setlow, "Spore germination," Curr. Opin. Microbiol., 6:550-556 (2003).
Shimanuki and Knox, "Diagnosis of honey bee diseases," U.S. Department of Agriculture, Beltsville, MD USA, (2000).
Shimanuki, "Identification and control of honey bee diseases," U.S. Dept. of Agriculture, Washington D.C. (1983).
Smith and Sullivan, "Germination of Clostridium cylindrosporum spores on medium containing uric acid," Appl. Environ. Microbiol., 55:1380-1385 (1989).
Sturtevant, "Relation of commercial honey to the spread of American Foulbrood," J. Agric. Res., 45:257 (1932).

(56) References Cited

OTHER PUBLICATIONS

Tarr, "Studies on American Foulbrood of bees," Ann. Appl. Biol., 25:807-814 (1938).
Warren and Gould, "Bacillus cereus spore germination: Absolute requirement for an amino acid," BBA-Gen. Subjects, 170:341-350 (1968).
White, "The bacteria of the apiary, with special reference to bee diseases," GPO, Washington (1906).
Winston, "The biology of the honey bee," Harvard University Press, Cambridge Massachusetts (1987).
Woese et al., "Analysis of action of L-alanine analogues in spore germination," J. Bacteriol., 76:578-588 (1958).
Yasuda-Yasaki et al., "Inhibition of Bacillus subtilis spore germination by various hydrophobic compounds: Demonstration of hydrophobic character of the L-alanine receptor site," J. Bacteriol., 136:484-490 (1978).
Yue et al., "Fluorescence in situ hybridization (FISH) analysis of the interactions between honeybee larvae and Paenibacillus larvae, the causative agent of American Foulbrood of honeybees (*Apis mellifera*)," Environ. Microbiol., 10:1612-1620 (2008).
Zimbro, 2009. Difco & BBL manual : Manual of microbiological culture media. Becton, Dickinson and Company, Sparks, MD.

* cited by examiner

Indole

Phenol 1 2 3 4 5

6 7 8 9 10

11 12 13 14 15

16 17 18 19 20

21 22 23 24 25

26 27 28 29

MODULATING GERMINATION OF *PAENIBACILLUS LARVAE*

CROSS-REFERENCE TO RELATED APPLICATIONS

This application claims benefit of priority from U.S. Provisional Application No. 61/919,224, filed on Dec. 20, 2013.

STATEMENT AS TO FEDERALLY SPONSORED RESEARCH

This invention was made with government support under NEVR-2010-03755 awarded by the United States Department of Agriculture. The government has certain rights in the invention. 2011-67013-30169 from the USDA/NIFA

TECHNICAL FIELD

This document relates to materials and methods for stimulating or inhibiting germination of *Paenibacillus larvae* spores, including methods for inhibiting *P. larvae* germination to reduce foulbrood in honey bees.

BACKGROUND

Honey bee pollination is crucial to a variety of crops, but honey bees are afflicted by a variety of pests and diseases. American foulbrood (AFB), a disease caused by *Paenibacillus larvae*, is arguably the most devastating of these diseases. AFB results in multi-million losses to the beekeeping industry, and is a likely contributing factor to Colony Collapse Disorder.

AFB kills developing honey bee larvae (White, "The bacteria of the apiary, with special reference to bee diseases," GPO, Washington, 1906; and Broodsgaard et al., *Apidologie* 29:569-578, 1998). *P. larvae* spores are the infectious agent for AFB, but it is the vegetative cells that cause disease (Genersch, *J. Invertebr. Pathol.,* 103:S10-S19, 2010; and Tarr, *Ann. Appl. Biol.,* 25:807-814, 1938).

In 2005, a survey of almond pollinating bee colonies indicated 4% of colonies had significant AFB load (Eischen and Graham, *Am. Bee. J.,* 145:390-391, 2005). Once a beekeeping operation is contaminated, the bacterial spores are not easily removed (Shimanuki, "Identification and control of honey bee diseases," U.S. Dept. of Agriculture, Washington D.C., 1983). Although autoclaving and high concentrations of chemical disinfectants effectively kill spores, these treatments are not viable for the bee keeping industry (Dobbelaere et al., *J. Appl. Microbiol.,* 91:212-216, 2001). In the United States, AFB typically is treated with prophylactic use of antibiotics (e.g., terramycin). However, the spore stage of *P. larvae* is not affected by antibiotic treatment, and the use of antibiotics can lead to resistant strains (Alippi, *Vet. Microbiol.,* 125:290-303, 2007; and Lodesani and Costa, *Bee World,* 86:102-109, 2005). Further, antibiotic treatment can leave residue in wax and honey, and many countries ban the use of antibiotics. Thus, burning of infected colonies and beekeeping equipment has been the only accepted practice for controlling the spread of AFB (Genersch, supra; and Shimanuki, supra).

SUMMARY

This document is based in part on the discovery that compounds such as indole and phenol can inhibit germination of *P. larvae* spores. In addition, this document provides materials and methods that can be used to inhibit (e.g., reduce or prevent) germination of *P. larvae* spores. For example, the materials and methods described herein can be used to reduce or prevent the rate of *P. larvae* spore germination, and thus can reduce the risk of developing *P. larvae*-associated disease or reduce existing *P. larvae*-associated disease. In some cases, for example, the materials and methods provided herein can be used to treat or prevent foulbrood in honey bees.

In one aspect, this document features a method for preventing germination of a *Paenibacillus larvae* spore. The method can include contacting the spore with:

(a) a compound of Formula (I):

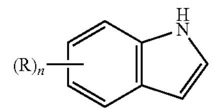

or a pharmaceutically acceptable salt thereof, where each R is independently selected from the group consisting of: substituted or unsubstituted $(C_1-C_6)$alkyl, substituted or unsubstituted $(C_2-C_6)$alkenyl, substituted or unsubstituted $(C_2-C_6)$alkynyl, halo, $(C_1-C_6)$haloalkyl, $OR^A$, $COR^A$, $COOR^A$, $OCOR^A$, CN, $NO_2$, $NR^AR^B$, and $NR^ACOR^B$; each $R^A$ and $R^B$ are independently selected from the group consisting of H and $(C_1-C_6)$alkyl; and n is an integer from 0 to 6; or (b) a compound of Formula (II):

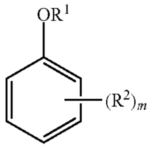

or a pharmaceutically acceptable salt thereof, where $R^1$ is selected from the group consisting of H and $(C_1-C_6)$alkyl; each $R^2$ is independently selected from the group consisting of: substituted or unsubstituted $(C_1-C_6)$alkyl, substituted or unsubstituted $(C_2-C_6)$alkenyl, substituted or unsubstituted $(C_2-C_6)$alkynyl, halo, $(C_1-C_6)$haloalkyl, $OR^A$, $COR^A$, $COOR^A$, $OCOR^A$, CN, $NO_2$, $NR^AR^B$, and $NR^ACOR^B$; each $R^A$ and $R^B$ are independently selected from the group consisting of H and $(C_1-C_6)$alkyl; and n is an integer from 0 to 5. The spore can be contacted with the compound in an amount effective to prevent germination of the spore.

The method can include contacting the spore with a compound of Formula (I), where n is 1; contacting the spore with a compound of Formula (I), where n is 1 and R is halo; contacting the spore with a compound of Formula (I), where R is a substituted or unsubstituted $(C_1-C_6)$alkyl; contacting the spore with a compound of Formula (I), where R is an unsubstituted $(C_1-C_6)$alkyl; or contacting the spore with a compound of Formula (I), where R is $CH_3$. The method can include contacting the spore with a compound of Formula (I), where the compound of Formula (I) is selected from the group consisting of:

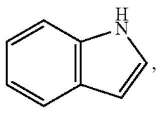, 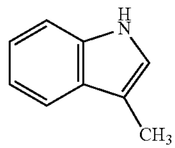,

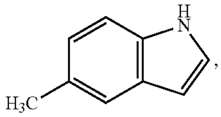, and 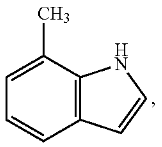, or a pharmaceutically acceptable salt thereof. The method can include contacting the spore with a compound of Formula (II), where n is 0, or contacting the spore with a compound of Formula (II), where $R^1$ is H. The method can include contacting the spore with a compound of Formula (II), where the compound of Formula (II) is:

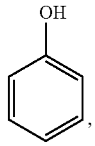, or a pharmaceutically acceptable salt thereof.

In another aspect, this document features a composition containing a carrier and:

(a) a compound of Formula (I):

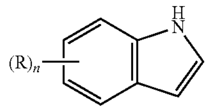

or a pharmaceutically acceptable salt thereof, where each R is independently selected from the group consisting of: substituted or unsubstituted $(C_1\text{-}C_6)$alkyl, substituted or unsubstituted $(C_2\text{-}C_6)$alkenyl, substituted or unsubstituted $(C_2\text{-}C_6)$alkynyl, halo, $(C_1\text{-}C_6)$haloalkyl, $OR^A$, $COR^A$, $COOR^A$, $OCOR^A$, CN, $NO_2$, $NR^AR^B$, and $NR^ACOR^B$; each $R^A$ and $R^B$ are independently selected from the group consisting of H and $(C_1\text{-}C_6)$alkyl; and n is an integer from 0 to 6; or (b) a compound of Formula (II):

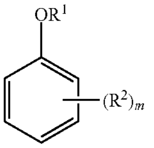

or a pharmaceutically acceptable salt thereof, where $R^1$ is selected from the group consisting of H and $(C_1\text{-}C_6)$alkyl; each $R^2$ is independently selected from the group consisting of: substituted or unsubstituted $(C_1\text{-}C_6)$alkyl, substituted or unsubstituted $(C_2\text{-}C_6)$alkenyl, substituted or unsubstituted $(C_2\text{-}C_6)$alkynyl, halo, $(C_1\text{-}C_6)$haloalkyl, $OR^A$, $COR^A$, $COOR^A$, $OCOR^A$, CN, $NO_2$, $NR^AR^B$, and $NR^ACOR^B$; each $R^A$ and $R^B$ are independently selected from the group consisting of H and $(C_1\text{-}C_6)$alkyl; and n is an integer from 0 to 5.

The composition can include a compound of Formula (I), where n is 1; a compound of Formula (I), where n is 1 and R is halo; a compound of Formula (I), where R is a substituted or unsubstituted $(C_1\text{-}C_6)$alkyl; a compound of Formula (I), where R is an unsubstituted $(C_1\text{-}C_6)$alkyl, or a compound of Formula (I), where R is $CH_3$. The composition can contain a compound of Formula (I), where the compound of Formula (I) is selected from the group consisting of:

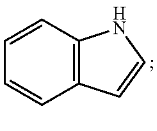; 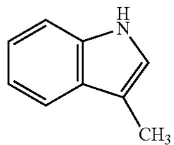;

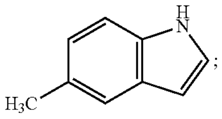; and 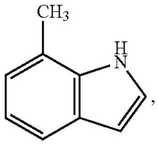, or a pharmaceutically acceptable salt thereof. The composition can contain a compound of Formula (II), where n is 0; or a compound of Formula (II), where $R^1$ is H. The composition can contain a compound of Formula (II), where the compound of Formula (II) is:

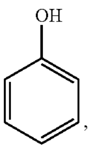, or a pharmaceutically acceptable salt thereof.

In another aspect, this document features a method for reducing germination of *Paenibacillus larvae* spores in honey bee larvae. The method can include administering to the honey bee larvae a composition comprising:

(a) a compound of Formula (I):

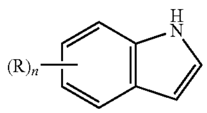

or a pharmaceutically acceptable salt thereof, where each R is independently selected from the group consisting of: substituted or unsubstituted $(C_1\text{-}C_6)$alkyl, substituted or unsubstituted $(C_2\text{-}C_6)$alkenyl, substituted or unsubstituted $(C_2\text{-}C_6)$alkynyl, halo, $(C_1\text{-}C_6)$haloalkyl, $OR^A$, $COR^A$, $COOR^A$, $OCOR^A$, CN, $NO_2$, $NR^AR^B$, and $NR^ACOR^B$; each $R^A$ and $R^B$ are independently selected from the group consisting of H and $(C_1\text{-}C_6)$alkyl; and n is an integer from 0 to 6; or (b) a compound of Formula (II):

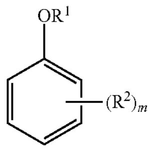

or a pharmaceutically acceptable salt thereof, where $R^1$ is selected from the group consisting of H and $(C_1-C_6)$alkyl; each $R^2$ is independently selected from the group consisting of: substituted or unsubstituted $(C_1-C_6)$alkyl, substituted or unsubstituted $(C_2-C_6)$alkenyl, substituted or unsubstituted $(C_2-C_6)$alkynyl, halo, $(C_1-C_6)$haloalkyl, $OR^A$, $COR^A$, $COOR^A$, $OCOR^A$, CN, $NO_2$, $NR^AR^B$, and $NR^ACOR^B$; each $R^A$ and $R^B$ are independently selected from the group consisting of H and $(C_1-C_6)$alkyl; and n is an integer from 0 to 5. The composition can be administered in an amount effective to reduce germination of *P. larvae* spores in the honey bee larvae.

The method can include administering a compound of Formula (I), where n is 1; administering a compound of Formula (I), where n is 1 and R is halo; administering a compound of Formula (I), where R is a substituted or unsubstituted $(C_1-C_6)$alkyl; administering a compound of Formula (I), where R is an unsubstituted $(C_1-C_6)$alkyl, or administering a compound of Formula (I), where R is $CH_3$. The method can include administering a compound of Formula (I), where the compound of Formula (I) is selected from the group consisting of:

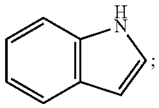 ; 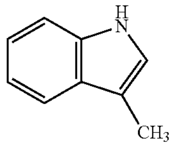 ;

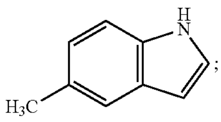 ; and 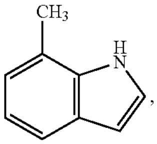 , or a pharmaceutically acceptable salt thereof. The method can include administering a compound of Formula (II), where n is 0; or administering a compound of Formula (II), where $R_1$ is H. The method can include administering a compound of Formula (II), where the compound of Formula (II) is:

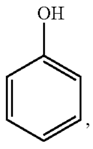 , or a pharmaceutically acceptable salt thereof.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 2A: *P. larvae* spores were suspended in 3 mM L-tyrosine/3 mM uric acid and individually exposed to temperatures between 25° C. and 42° C. The maximum germination rate was set to 100% for spores germinated at 42° C. Percent germination for other conditions was calculated relative to 42° C. Error bars represent standard deviations from at least six independent measurements. Columns not connected by the same letter are statistically different ($p>0.05$). FIG. 2B: *P. larvae* spores were suspended in 3 mM L-tyrosine/3 mM uric acid and individually exposed to pH values between 3 and 9. The maximum germination rate was set to 100% for spores germinated at pH 7. Percent germination for other conditions was calculated relative to pH 7. Error bars represent standard deviations from at least six independent measurements. Columns not connected by the same letter are statistically different ($p>0.05$).

FIG. 3A: Dose response curve for *P. larvae* spores germinated at saturating concentration of uric acid and various concentrations of L-tyrosine. The $EC_{50}$ for L-tyrosine was determined based on these data. FIG. 3B: Dose response curve for *P. larvae* spores germinated at saturating concentration of L-tyrosine and various concentrations of uric acid. The $EC_{50}$ for uric acid was determined based on these data.

FIG. 4A: Dose response curve for *P. larvae* spores germinated with L-tyrosine/uric acid in the presence of various concentrations of indole. The $IC_{50}$ for indole was determined based on these data. FIG. 4B: Dose response curve for *P. larvae* spores germinated with L-tyrosine/uric acid in the presence of various concentrations of phenol. The $IC_{50}$ for phenol was determined based on these data.

6-Nitrobenzothiazole 12. Allopurinol; 13. Saccharin; 14. 2-Aminophenol; 15. 2-Mercaptopyridine; 16. 2-Mercaptopyrimidine; 17. 3-Aminophenol; 18. Nicotinic acid; 19. 1-Acetylindole; 20. 2-oxoindole; 21. 3-Cyanoindole; 22. 4-Cyanoindole; 23. 5-Fluoroindole; 24. 5-hydroxyindole; 25. 5-Chloroindole; 26. 6-Aminoindole; 27. 6-chloroincole; 28. 6-Fluoroindole; 29. 3-Ethanamineindole.

Figure 6A:
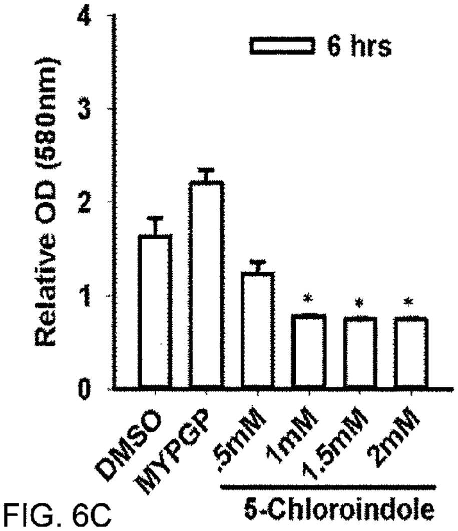
Figure 6B:
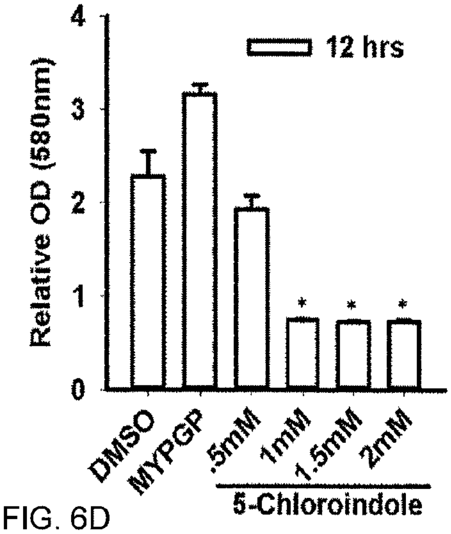
Figure 6C:
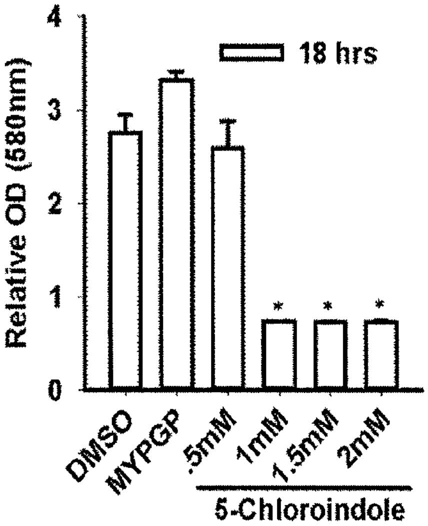
Figure 6D:
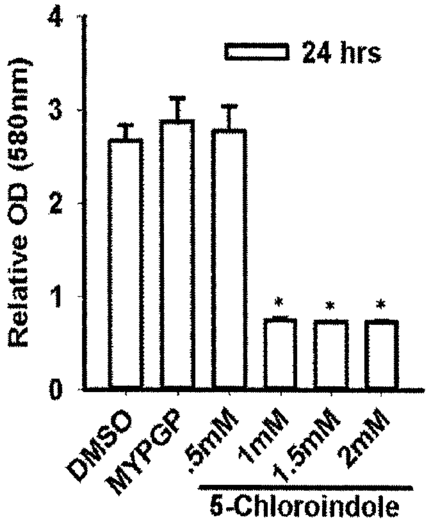

FIGS. 6A-6D are graphs plotting the inhibition activity of 5-chloroindole on *P. larvae* cells. *P. larvae* cells were grown in medium containing different concentrations of 5-chloroindole, and cellular growth was monitored over a 24 hour period. Graphs are shown for 6 hours (FIG. 6A), 12 hours (FIG. 6B), 18 hours (FIG. 6C), and 24 hours (FIG. 6D). Asterisks denote significant differences from the growth of medium control (Analysis of Variance, Log-rank test, $p<0.05$).

Figure 7A:
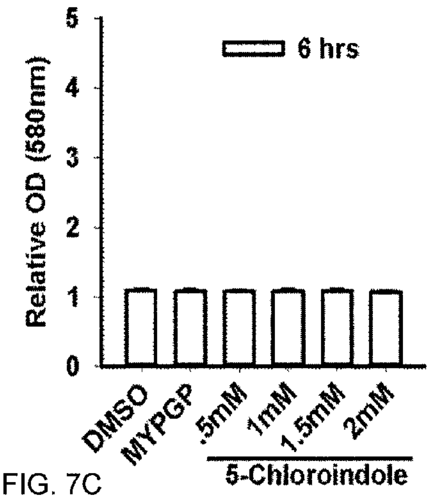
Figure 7B:
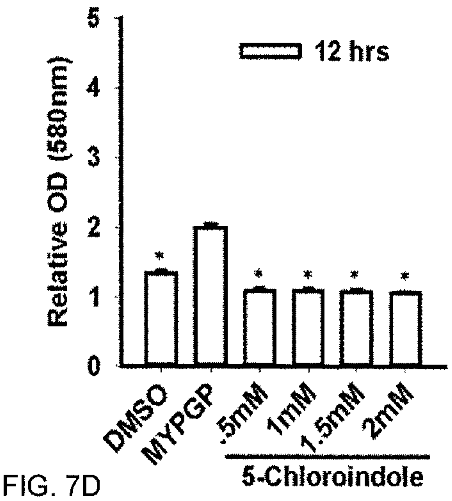
Figure 7C:
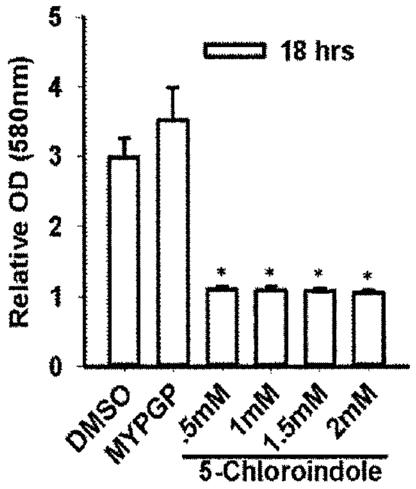
Figure 7D:
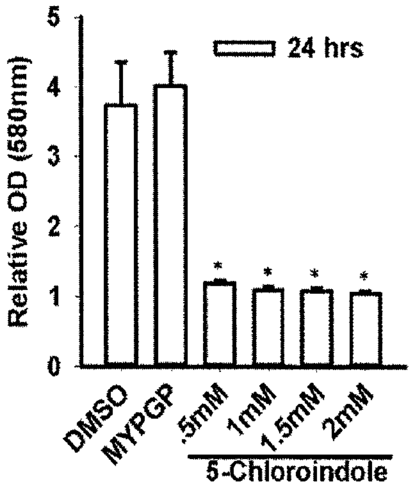

FIGS. 7A-7D are graphs plotting the inhibition activity of 5-chloroindole on *P. larvae* spores. *P. larvae* spores were grown in medium containing different concentrations of 5-chloroindole. Growth was monitored over a 24 hour period; plots are shown for 6 hours (FIG. 7A), 12 hours (FIG. 7B), 18 hours (FIG. 7C), and 24 hours (FIG. 7D). Asterisks denote significant differences from the growth of medium control (Analysis of Variance, Log-rank test, $p<0.05$).

Figure 8B:
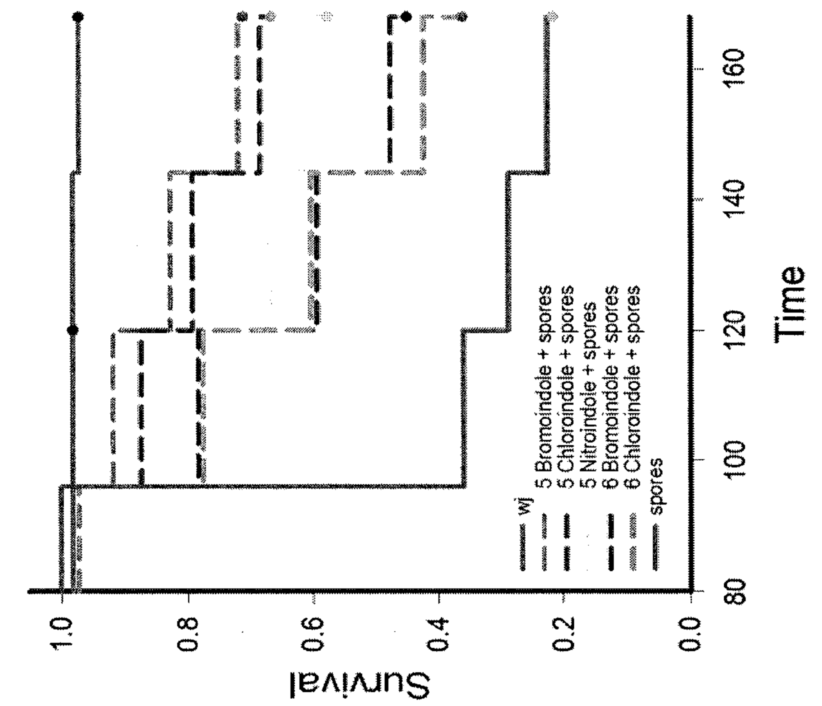
Figure 8A:
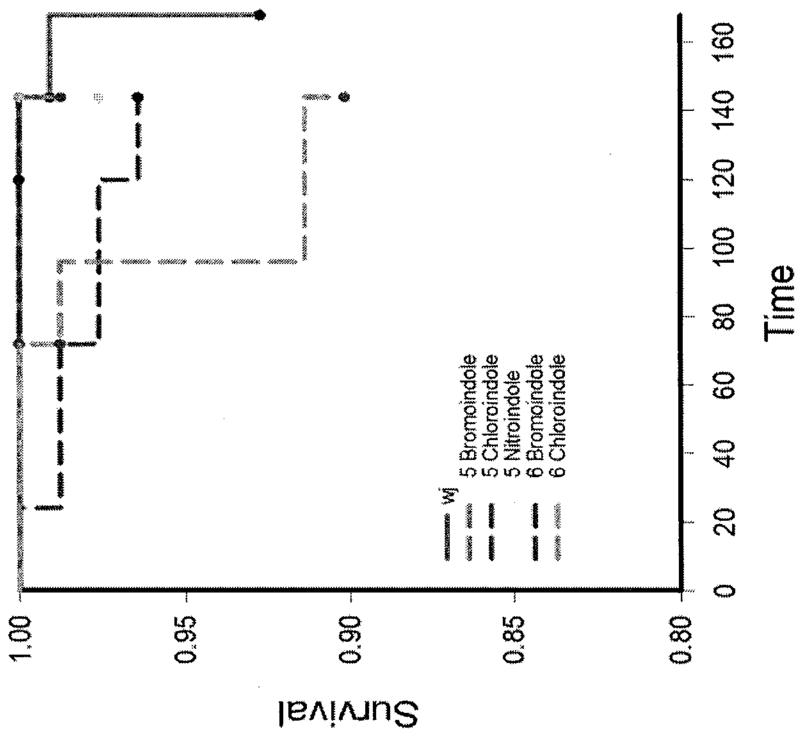

FIGS. 8A and 8B are graphs plotting larval survival during the 7-day development stage of honey bee larvae. FIG. 8A shows survival curves for honey bee larvae fed larval diet (wj) supplemented with 0.5 mM of the indicated indole analogues. FIG. 8B shows survival curves for honey bee larvae fed larval diet (wj) supplemented with the indicated 0.5 mM indole analogues and *P. larvae* spores. Differences between survival curves were determined using Kaplan-Meier analysis and Log-Rank test ($p<0.002$).

Figure 9B:
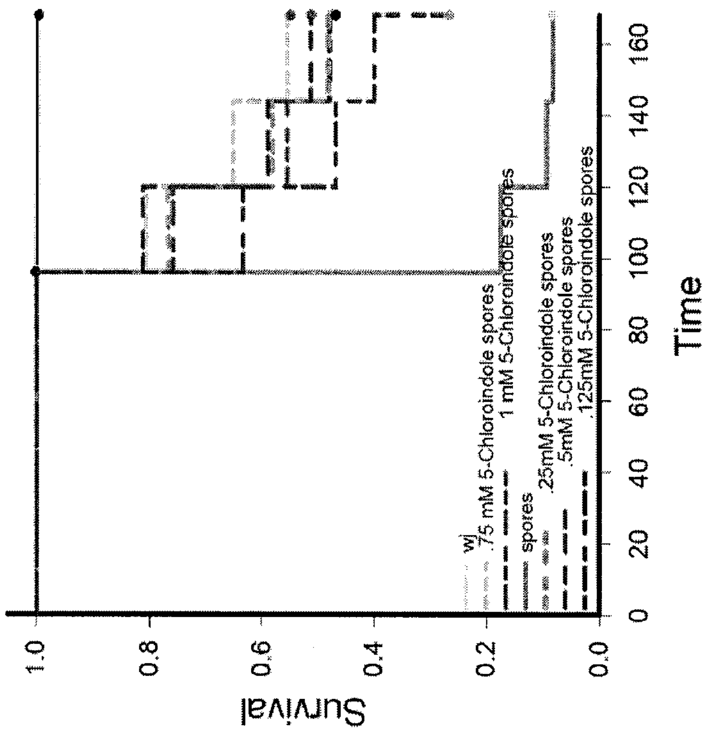
Figure 9A:
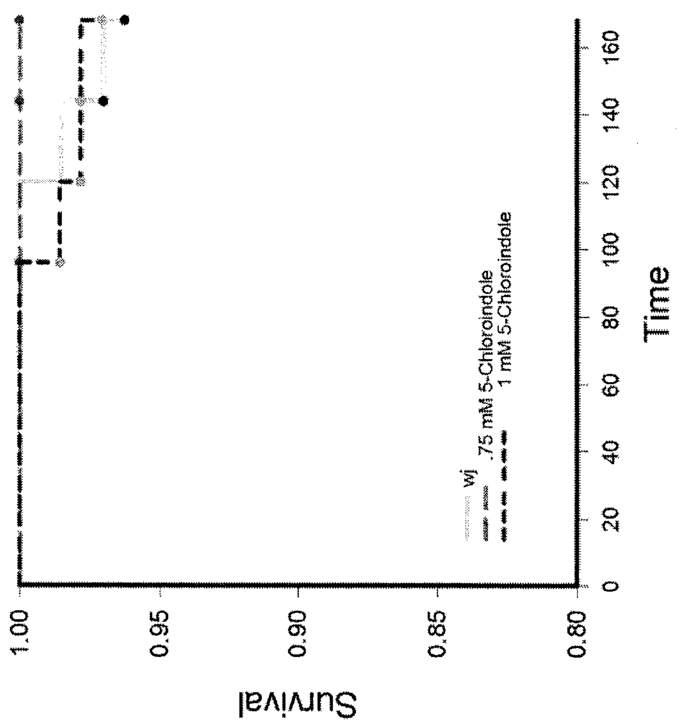

FIGS. 9A and 9B are graphs plotting larval survival during the 7-day development stage of honey bee larvae. FIG. 9A shows survival curves for honey bee larvae fed larval diet (wj) supplemented with 0.75 and 1 mM 5-chloroindole. FIG. 9B shows survival curves of honey bee larvae fed larval diet (wj) supplemented with different concentrations of 5-chloroindole and *P. larvae* spores. Differences between survival curves were determined using Kaplan-Meier analysis and Log-Rank test ($p<0.001$).

DETAILED DESCRIPTION

AFB occurs when first or second instar larvae (within 48 hours after the egg hatches) ingest food contaminated with bacterial spores (Crailsheim and Riessberger-Galle, *Apidologie,* 32:91-103, 2001). Twelve hours after ingestion, *P. larvae* spores germinate, and the new vegetative cells begin proliferating inside the larval gut (Yue et al., *Environ. Microbiol.,* 10:1612-1620, 2008). Several days post-infection, bacteremia causes the death of the honey bee larva (Davidson, *J. Invertebr. Pathol.,* 21:53-61, 1973; Genersch et al., *Appl. Environ. Microbiol.,* 71:7551-7555, 2005; and Genersch et al., *Int. J. Syst. Evol. Microbiol.,* 56:501-511, 2006). After nutrients are depleted, *P. larvae* cells stop dividing and sporulate. As a result, billions of spores are found in the remains of each bee larva (Lindstrom et al., *J. Invertebr. Pathol.,* 99:82, 2008; and Sturtevant, *J. Agric. Res.,* 45:257, 1932). Spores are transmitted within the colony by adult bees that eat larval remains (Fries and Camazine, *Apidologie,* 32:199-214, 2001; and Gillard et al., *J. Invertebr. Pathol.,* 99:92-95, 2008). In addition, *P. larvae* spores can be transmitted between colonies by contaminated beekeeping equipment, and by robbing of honey from infected colonies by neighboring bees (Fries et al., *Vet. Microbiol.,* 114:269-274, 2006).

The environmental cues required to trigger *P. larvae* spore germination have not previously been elucidated. As described herein, experiments conducted to test the ability of various compounds to promote or inhibit *P. larvae* spore germination showed that *P. larvae* spores can recognize L-tyrosine and uric acid as co-germinants, while indole and phenol (the side chains of tryptophan and tyrosine), and several derivatives thereof, can inhibit germination.

This document provides, *inter alia*, materials and methods that can be used to inhibit (e.g., reduce or prevent) germination of *P. larvae* spores. For example, the materials and methods described herein can be used to reduce or prevent the rate of *P. larvae* spore germination, and thus can reduce the risk of developing *P. larvae*-associated disease or reduce existing *P. larvae*-associated disease. In some cases, such materials and methods can be used to treat or prevent foulbrood in honey bees, and can include administering to a subject (e.g., a honey bee larva) an effective amount of a germination-inhibiting compound derived from phenol or indole. The compound derived from indole or phenol can have a central core structure of the formula:

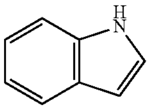
or
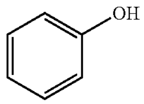

As used herein, the term "disease" refers to any abnormal condition that impairs physiological function and is associated with specific symptoms. The term is used broadly to encompass any disorder, illness, abnormality, pathology, sickness, condition or syndrome in which physiological function is impaired, irrespective of the nature of the etiology (or even whether the etiological basis for the disease is established).

As used herein, the term "*P. larvae*-associated disease" refers to any disease that involves (e.g., is caused, exacerbated, associated with, or characterized by the presence of) *P. larvae* residing and/or replicating in the body of a subject. Thus, the term encompasses any disease, disorder, pathology, symptom, clinical condition, or syndrome in which bacteria of the species *P. larvae* act as etiological agents or in which infection with one or more strains of *P. larvae* is implicated, detected or involved.

The terms "treatment" and "treating" refer to an intervention (e.g., the administration of an agent to a subject) that prevents, slows, or delays the onset or progression of a disease or reduces (e.g., eradicates) its incidence within a treated subject (e.g., a honey bee).

The term "minimum inhibitory concentration" or "MIC" defines the lowest concentration of a test compound that is needed to inhibit germination of a spore in vitro or in vivo. A common method for determining the MIC of an antibiotic is to prepare several tubes containing serial dilutions of the test compound that are then inoculated with the bacterial isolate of interest. Following incubation at appropriate atmosphere and temperature, the MIC of an antibiotic can be determined from the tube with the lowest concentration that shows no turbidity.

As used herein, an "effective amount," "therapeutically effective amount," or "prophylactically effective amount" of a compound is an amount that is sufficient to provide the desired effect (e.g., treatment or prophylaxis manifested by a permanent or temporary improvement in a subject's condition, such as reduced germination of *P. larvae* spores in honey bee larvae), and that can be administered without excessive toxicity, irritation, allergic response, or other problem or complication, commensurate with a reasonable benefit/risk ratio. Standard dosing techniques can be used to determine an appropriate "effective" amount for use in a subject or population of subjects. In some cases, for example, an effective amount of a compound as described herein can include the MIC of that compound or an amount at least 10 percent higher than the MIC (e.g., an amount 10 to 150 percent, 10 to 125 percent, 10 to 100 percent 10 to 75 percent, 20 to 150 percent, 30 to 150 percent, 30 to 100 percent, 50 to 150 percent, or 50 to 100 percent higher than the MIC). In some embodiments, an effective amount can include at least the $IC_{50}$ for that compound (see, e.g., the Examples below), or an amount at least 10 percent higher than the $IC_{50}$ (e.g., an amount 10 to 150 percent, 10 to 125 percent, 10 to 100 percent 10 to 75 percent, 20 to 150 percent, 30 to 150 percent, 30 to 100 percent, 50 to 150 percent, or 50 to 100 percent higher than the $IC_{50}$).

Pharmaceutically acceptable derivatives as applied to the compounds provided herein are compounds that are obtained (or obtainable) by chemical derivatization of a parent compound (e.g., indole or phenol). Pharmaceutically acceptable derivatives are therefore suitable for administration to or use in contact with mammalian tissues without undue toxicity, irritation or allergic response (i.e., commensurate with a reasonable benefit/risk ratio). Derivatives can be obtained (or obtainable) by, for example, alkylation, esterification, or acylation of parent compounds. Derivatives may be active per se, or may be inactive until processed in vivo. In the latter case, the derivatives can act as prodrugs (e.g., covalently bonded compounds that release the active parent drug after cleavage of the covalent bond(s) in vivo). Pharmaceutically acceptable derivatives typically retain some or all of the activity of the parent compound. In some cases, activity can be increased by derivatization. Derivatization also can augment other biological activities of the parent compound, such as bioavailability.

The term "pharmaceutically acceptable salt" refers to the relatively non-toxic, inorganic and organic acid addition salts of a compound provided herein. These salts can be prepared in situ during the final isolation and purification of a compound provided herein, or by separately reacting the compound in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, laurylsulphonate salts, and amino acid salts, and the like. See, for example, Berge et al., *J. Pharm. Sci.,* 66:1-19, 1977.

In some embodiments, a compound provided herein may contain one or more acidic functional groups and, thus, is capable of forming pharmaceutically acceptable salts with pharmaceutically acceptable bases. The term "pharmaceutically acceptable salts" in these instances refers to the relatively non-toxic inorganic and organic base addition salts of a compound provided herein. These salts can likewise be prepared in situ during the final isolation and purification of the compound, or by separately reacting the purified compound in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

The term "pharmaceutically acceptable solvate" as applied to the compounds provided herein defines any pharmaceutically acceptable solvate form of a specified compound that retains the biological effectiveness of such compound. Examples of solvates include compounds in combination with water (hydrates), isopropanol, ethanol, methanol, dimethyl sulfoxide, ethyl acetate, acetic acid, ethanolamine, or acetone. Also included are miscible formulations of solvate mixtures, such as a compound in combination with an acetone and ethanol mixture. In some embodiments, a solvate can include a compound in combination with about 20% ethanol and about 80% acetone. Thus, the structural formulae include compounds having the indicated structure, including the hydrated as well as the non-hydrated forms.

The term "pharmaceutically acceptable prodrug" as applied to the compounds described herein defines any pharmaceutically acceptable compound that can be converted under physiological conditions or by solvolysis to the specified compound, to a pharmaceutically acceptable salt of such compound, or to a compound that shares at least some of the activity of the specified compound (e.g., exhibiting activity against germination of *P. larvae* spores).

The term "pharmaceutically acceptable metabolite" as applied to the compounds described herein defines a pharmacologically active product produced through metabolism in the body of the specified compound or salt thereof.

Prodrugs and active metabolites of the compounds useful in the methods described herein can be identified using routine techniques known in the art (see, for example, Bertolini et al., *J. Med. Chem.,* 40:2011-2016, 1997).

The term "pharmaceutically acceptable complex" as applied to the compounds provided herein defines compounds or compositions in which the compound forms a component part. Such complexes include derivatives in which a compound as described herein is physically associated (e.g., by covalent or non-covalent bonding) to another moiety or moieties. The term therefore includes multimeric forms of the compounds provided herein. Such multimers can be generated by linking or placing multiple copies of a compound in close proximity to each other (e.g., via a scaffolding or a carrier moiety).

In some embodiments, this document provides methods for preventing germination of a *P. larvae* spore. The methods can include contacting a *P. larvae* spore with an amount of indole, phenol, or a derivative thereof (e.g., a compound of Formula (I) or Formula (II) as described herein) that is effective to prevent germination of the spore. In some embodiments, the spore can be contacted in vitro, such as by including indole, phenol, or a derivative thereof in a culture medium containing the spore. In some embodiments, the methods provided herein can be used for inhibiting germination of *P. larvae* spores in vivo (e.g., in honey bee larvae). Thus, in some cases, the method can include providing honey bee larvae with a composition (e.g., a nutritional medium such as worker jelly or royal jelly) containing an amount of indole, phenol, or a derivative thereof, that is effective to prevent germination of *P. larvae* spores. Nutritional media for honey bees can be obtained commercially, for example, and supplemented with a compound as described herein.

In some embodiments, a method for inhibiting germination of *P. larvae* spores can include contacting one or more spores with a compound of Formula (I):

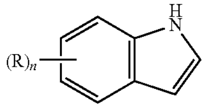

(I)

or a pharmaceutically acceptable salt thereof. Each R can be independently selected from the group consisting of: substituted or unsubstituted ($C_1$-$C_6$)alkyl; substituted or unsubstituted ($C_2$-$C_6$)alkenyl; substituted or unsubstituted ($C_2$-$C_6$)alkynyl; halo; ($C_1$-$C_6$)haloalkyl; $OR^A$; $COR^A$; $COOR^A$; $OCOR^A$; CN; $NO_2$; $NR^AR^B$; and $NR^ACOR^B$. Each $R^A$ and $R^B$ can be independently selected from the group consisting of H and ($C_1$-$C_6$)alkyl. N can be an integer from 0 to 6 (e.g., 0, 1, 2, 3, 4, 5, or 6). In some embodiments, for example, R can be a substituted or unsubstituted ($C_1$-$C_6$)alkyl (e.g., $CH_3$). Thus, in some embodiments, the methods provided herein can include contacting one or more *P. larvae* spores with a compound selected from the group consisting of:

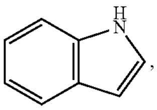,
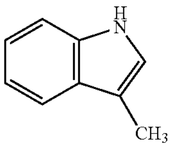,
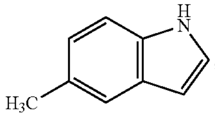, and
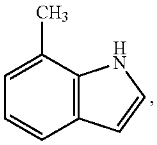, or a pharmaceutically acceptable salt thereof.

In some embodiments, a method for inhibiting germination of *P. larvae* spores can include contacting one or more spores with a compound of Formula (II):

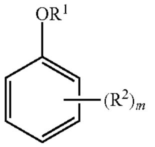

or a pharmaceutically acceptable salt thereof. $R^1$ can be selected from the group consisting of H and ($C_1$-$C_6$)alkyl. Each $R^2$ can be independently selected from the group consisting of: substituted or unsubstituted ($C_1$-$C_6$)alkyl; substituted or unsubstituted ($C_2$-$C_6$)alkenyl; substituted or unsubstituted ($C_2$-$C_6$)alkynyl; halo; ($C_1$-$C_6$)haloalkyl; $OR^A$; $COR^A$; $COOR^A$; $OCOR^A$; CN; $NO_2$; $R^AR^B$; and $NR^ACOR^B$. Each $R^A$ and $R^B$ can be independently selected from the group consisting of H and ($C_1$-$C_6$)alkyl. N can be an integer from 0 to 5 (e.g., 0, 1, 2, 3, 4, or 5). In some embodiments, the methods provided herein can include contacting one or more *P. larvae* spores with the compound:

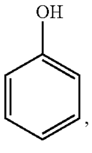, or a pharmaceutically acceptable salt thereof.

As used herein, the term "$C_{x-y}$alkyl" refers to saturated hydrocarbon groups, including straight-chain alkyl and branched-chain alkyl groups that contain from x to y carbons in the chain. The terms "$C_{2-y}$alkenyl" and "$C_{2-y}$alkynyl" refer to unsaturated aliphatic groups analogous in length to the alkyls described above, but that contain at least one double or triple bond, respectively.

As used herein, "halo" is a chloro, bromo, fluoro or iodo atom radical.

As used herein, "haloalkyl" means a hydrocarbon substituent, which is a linear or branched alkyl substituted with one or more chloro, bromo, fluoro, and/or iodo atom(s). In some embodiments, haloalkyls are of 1 to about 3 carbons in length. For example, a haloalkyl can be $CF_3$.

The term "substituted" refers to moieties having substituents replacing a hydrogen on one or more non-hydrogen atoms of the molecule. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. Substituents can include, for example, an alkyl, an alkene, an alkyne, a halo, a hydroxyl, a carbonyl (such as a carboxyl, an alkoxycarbonyl, a formyl, or an acyl), an alkoxyl, an amino, an amido, an amidine, an imine, a cyano, a nitro, or an azido, moiety. It will be understood by those skilled in the art that the moieties substituted on the hydrocarbon chain can themselves be substituted, if appropriate.

This document also provides compositions containing one or more compounds described herein (e.g., indole, phenol, or a derivative thereof) in combination with a carrier. Suitable carriers include, without limitation, water, buffered water, saline (e.g., 0.8% saline), glycine (e.g., 0.3% glycine), hyaluronic acid, and the like. The compositions also may contain auxiliary substances such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, sodium hydroxide, etc.

The invention will be further described in the following examples, which do not limit the scope of the invention described in the claims.

EXAMPLES

Example 1

Requirements for In Vitro Germination of *Paenibacillus larvae* Spores

Materials and Methods

Materials:

Chemicals were purchased from Sigma Aldrich Corporation (St. Louis, Mo.). Dehydrated culture media was purchased from BD Difco (Franklin Lakes, N.J.). *Paenibacillus larvae* subsp. *pulvifaciens* strain ATCC 49843 was purchased from the American Tissue Culture Collection (ATCC). Environmental American Foulbrood scales (the remains of infected larvae collected from infected hives) were kindly donated by Dr. Jay D. Evans at the USDA Bee Research Facility in Beltsville, Md. The environmental strain was identified as a strain of *Paenibacillus larvae* subsp. *larvae* based on its phenotypic characteristics and 16S rRNA analysis (Piccini et al., *World J. Microb. Biot.,* 18:761-765, 2002).

*P. larvae Spore* Preparation:

*P. larvae* strains were grown on BD tryptic soy agar plates for 7 days in a 5% $CO_2$ incubator at 37° C. The resulting bacterial lawns were collected by flooding with ice-cold deionized water. Spores were pelleted by centrifugation and resuspended in fresh deionized water. After three washing steps, spores were separated from vegetative and partially sporulated forms by centrifugation through a 20%-50% HistoDenz gradient. The spore pellet was washed five times with water and stored at 4° C. (Akoachere et al., *J. Biol. Chem.,* 282:12112-12118, 2007). Spore preparations were more than 90% pure as determined by microscopic observation of Schaeffer-Fulton stained samples (Schaeffer and Fulton, *Science* 77:194-194, 1933).

Preparation of Germinant Solution:

Sixteen complex media (MYPGP, TSB, BHI, Nutrient, LB, TMYGP, NZ amine, NZCYM, Lactobacillus, SOC, Bailey, Clostridium, Michael, Terrific, MD, and J broths) were prepared (Bailey and Lee, *J. Gen. Microbiol.,* 29:711-717, 1962; Dingman and Stahly *Appl. Environ. Microbiol.,* 46:860-869, 1983; and Zimbro, *Difco & BBL manual: Manual of microbiological culture media*. Becton, Dickinson and Company, Sparks, Md., 2009). A defined medium was prepared as previously described (Ramirez and Abel-Santos, *J. Bacteriol.,* 192:418-425, 2010). An artificial worker jelly (AWJ) medium was prepared based on modifications to the published composition of worker jelly (Rembold and Dietz, *Vitam. Horm.,* 23:359-382, 1966). For AWJ, the following stock solutions were prepared: 100 mM inosine in 220 mM NaOH, 400 mM for each sugar (fructose, glucose, and arabinose) in water, 30 mM for each of the 20 proteinogenic L-amino acids in 0.36 N HCl, 100 mM uric acid in 220 mM NaOH and 0.2 mg/ml vitamins (thiamine, riboflavin, pyridoxine, β-alanine, para-aminobenzoic acid, nicotinic acid, pantothenic acid, biotin, folic acid, and inositol) in water. To prepare AWJ, inosine, uric acid, sugars, and amino acids were dissolved to 3 mM final concentration in 0.1 M sodium phosphate buffer (0.06 mM $Na_2HPO_4$ and 0.04 mM $NaH_2PO_4$) and adjusted to pH 7.0. This solution was supplemented with vitamins to 1 μg/ml final concentration.

Determination of Germinants for *P. larvae* Spores:

The decrease in optical density is proportional to spore germination (Powell, *J. Gen. Microbiol.,* 4:330-338, 1950). Changes in light diffraction during spore germination were monitored at 580 nm ($OD_{580}$) on a Biomate 5 (ThermoElectron Corporation, Waltham, Mass.) or a Tecan Infinite m200 (Tecan group, Männedorf, Switzerland) spectrophotometer. Experiments were carried out in 96-well plates (200 μL/well). In preparation for germination assays, *P. larvae* spore suspensions were washed three times with water. Spores were then heat activated at 70° C. for 30 minutes. The heat-activated spores were allowed to reach room temperature and transferred to 0.1 M sodium phosphate buffer (pH 7.0) to an approximate $OD_{580}$ of 0.70. Spores were monitored for auto-germination for 30 minutes. Germination experiments were carried out with spores that did not auto-germinate. Putative germinants were added individually or in combinations to a final concentration of 3 mM. Experiments were performed in triplicate with at least two different spore preparations. After germinant addition, $OD_{580}$ of the spore suspension was measured every minute for an hour. Relative OD values were derived by dividing each $OD_{580}$ reading by the initial $OD_{580}$. Spore germination rates (v) were calculated from the initial linear decrease in relative OD (Akoachere et al., supra). Germination rates were set to 100% for *P. larvae* spores that had the fastest germination rate in an assay. Germination rates for other conditions were divided by the maximum germination rate for that assay and are reported as percent germination. Standard deviations were calculated from at least six independent measurements and are typically below 10%. Spore germination was confirmed in selected samples by microscope observation of Schaeffer-Fulton stained aliquots (Schaeffer and Fulton, supra).

Effect of Temperature and pH on *P. larvae* Germination:

For temperature experiments, *P. larvae* spores were germinated in 3 mM L-tyrosine and 3 mM uric acid. Germination rates were determined as described above, except that the germination temperature was varied between 25° C. and 42° C. The germination rate was set to 100% for spores germinated at 42° C. Germination rates for other conditions were divided by the maximum germination rate at 42° C., and are reported as percent germination. Germination rate differences were analyzed using ANOVA followed by a Tukey-Kramer procedure (SigmaPlot v.9).

For pH experiments, *P. larvae* spores were re-suspended in 0.1 M sodium phosphate, potassium/sodium phosphate, or citrate phosphate buffer. The pH of the buffers was adjusted between 3.0 and 9.0. Spores were germinated in the presence of 3 mM L-tyrosine and 3 mM uric acid. Germination rates were determined as described above. The germination rate was set to 100% for spores germinated at pH 7.0. Germination rates for other conditions were divided by the maximum germination rate at pH 7, and are reported as percent germination. As above, germination rate differences were analyzed using ANOVA followed by a Tukey-Kramer procedure (SigmaPlot v.9).

Activation of *P. larvae* Spore Germination by L-Tyrosine and Uric Acid:

*P. larvae* spore germination was tested with different combinations of L-tyrosine and uric acid. For L-tyrosine titrations, spores were exposed to varying concentrations of L-tyrosine and a constant 3 mM uric acid. For uric acid titrations, spores were exposed to varying concentrations of uric acid and a constant 3 mM L-tyrosine. Germination rates were determined as above. The germination rate was set to 100% for *P. larvae* spores germinated in the presence of 3 mM L-tyrosine/3 mM uric acid. Germination rates for other conditions were divided by the maximum germination rate obtained with 3 mM L-tyrosine/3 mM uric acid, and are reported as percent germination. Percent germination was plotted against compound concentrations. The resulting sigmoidal curves were fitted using the four parameter logistic function of the SigmaPlot v.9 software to calculate $EC_{50}$ values (for enhancers of spore germination). $EC_{50}$ is defined as the concentration of a germinant required to increase the germination rate to 50% of the maximal value (Rodbard et al., *Clin. Chem.,* 22:350-358, 1976; and Sebaugh, *Pharm. Stat.,* 10:128-134, 2011).

Agonists of *P. larvae* Spore Germination:

To test for possible agonists of *P. larvae* spore germination, spores were individually supplemented with 3 mM of a purine analog and 3 mM L-tyrosine. Separately, *P. larvae* spores were incubated with 3 mM of an amino acid analog and 3 mM uric acid. Spore germination was monitored as described above. Germination rates for other conditions were divided by the maximum germination rate obtained with 3 mM L-tyrosine/3 mM uric acid, and are reported as percent germination.

Antagonists of *P. larvae* Spore Germination:

To test for possible antagonists of *P. larvae* spore germination, spores were individually supplemented with 3 mM of a purine analog or 3 mM of an amino acid analog. Spore suspensions were incubated for 15 minutes at room temperature while monitoring OD580. If no germination was detected, L-tyrosine and uric acid were added to 3 mM final concentrations, and germination was monitored as described above. Germination rates for other conditions were divided by the uninhibited maximum germination rate obtained with 3 mM L-tyrosine/3 mM uric acid, and are reported as percent germination.

Inhibition of *P. larvae* Spore Germination by Indole and Phenol:

*P. larvae* spores were individually incubated with varying concentrations of indole, phenol, 1-N-methylindole, 3-mehtylindole, 5-methylindole, or 7-methylindole. After 15 minutes of incubation, spores were treated with 3 mM L-tyrosine/3 mM uric acid. The germination rate was set to 100% for *P. larvae* spores germinated in the absence of inhibitor. Germination rates for other conditions were divided by the uninhibited maximum germination rate obtained with 3 mM L-tyrosine/3 mM uric acid, and are reported as percent germination. Percent germination was plotted against inhibitor concentrations. The resulting sigmoidal curves were fitted using the four parameter logistic function in SigmaPlot v.9 to calculate $IC_{50}$ values. $IC_{50}$ is the concentration of a germination inhibitor required to reduce the germination rate to 50% of the maximal value (Akoachere et al., supra; and Rodbard et al., supra).

*P. larvae* Spore Germination in Various Media

Figure 1:
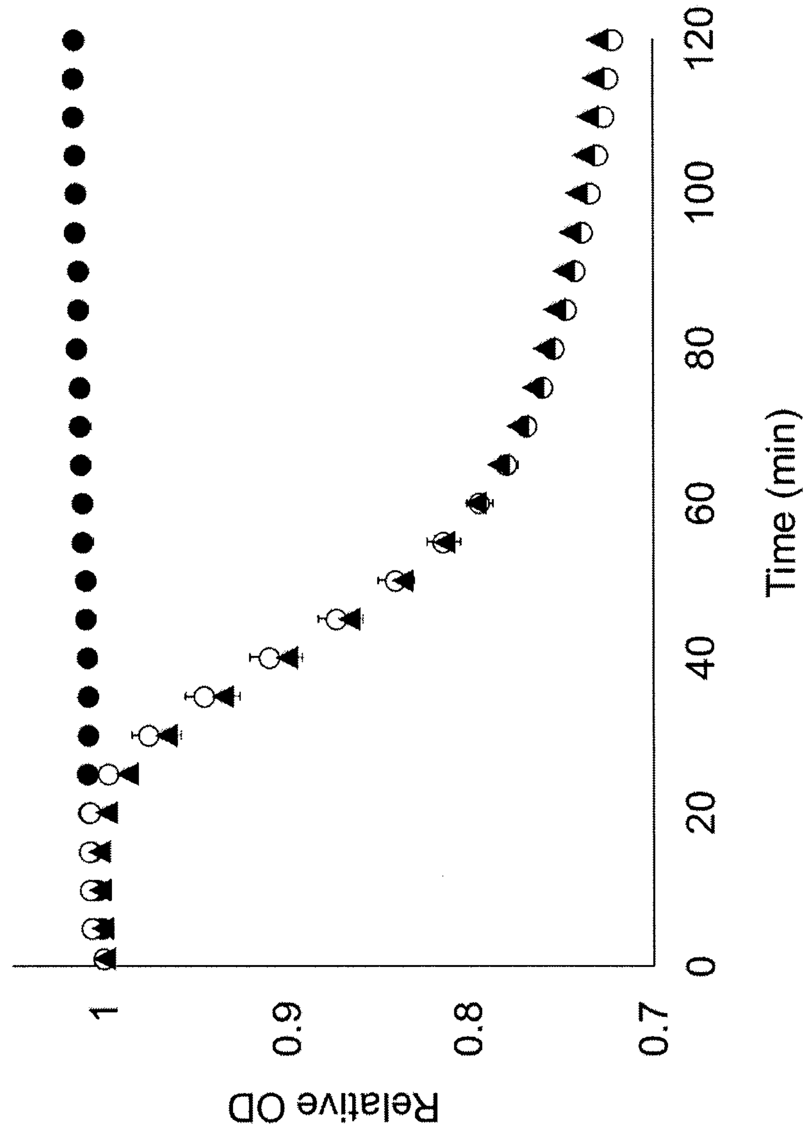
FIG. 1 is a graph plotting germination of *P. larvae* strain ATCC49843 spores in defined medium (●), artificial worker jelly (○), or uric acid plus L-tyrosine (▲). Data are shown every five minutes. Spore germination was followed by the decrease of relative OD over time. Error bars represent standard deviations from at least six independent measurements.

No significant *P. larvae* spore germination was detected in any of the 16 different complex media tested, even after 24 hours of incubation. In comparison, spores of *Bacillus anthracis* and *Bacillus cereus* germinate within two hours in rich medium (Johnson et al., *J. Food Sci.,* 48:286-287, 1983; and Sanz et al., *Infect. Immun.,* 76:1036-1047, 2008). Similarly, *P. larvae* spores failed to germinate in defined medium containing metabolites commonly used as germinants by *Bacillus* and *Clostridia* species (FIG. 1).

Honey bee larvae are fed royal or worker jelly, which can be contaminated with *P. larvae* spores (41. Winston, *The biology of the honey bee*, Harvard University Press, Cambridge, Mass., 1987). *P. larvae* spores were resuspended in a chemically defined medium (AWJ) that differs from worker jelly only in its pH value. The optical density of *P. larvae* spores suspended in AWJ decreased, indicating that the spores were germinating (FIG. 1). Spore germination was confirmed by Schaeffer-Fulton staining.

Compounds Required for *P. larvae* Spore Germination

To identify compounds necessary to trigger *P. larvae* spore germination, groups of compounds were systematically omitted from the AWJ medium. *P. larvae* spores germinated well in the absence of sugars and vitamins, suggesting that germination onset required uric acid and proteinogenic amino acid(s). The testing of individual amino acids showed that only L-tyrosine was able to synergize with uric acid to produce a strong germination response in *P. larvae* spores (FIG. 1). A mixture of uric acid and the remaining 19 proteinogenic amino acids induced negligible germination response.

Effects of Temperature on *P. larvae* Spore Germination

Figure 2A:
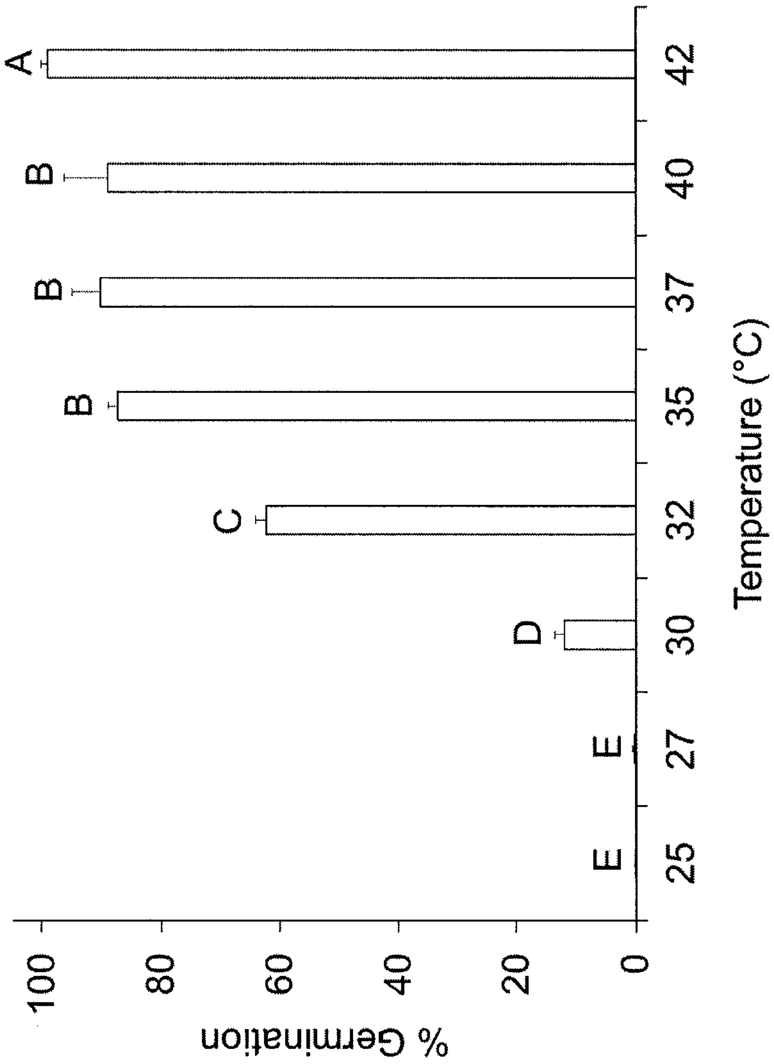
FIGS. 2A and 2B are graphs plotting the effect of temperature and pH on *P. larvae* spore germination.
Figure 2B:
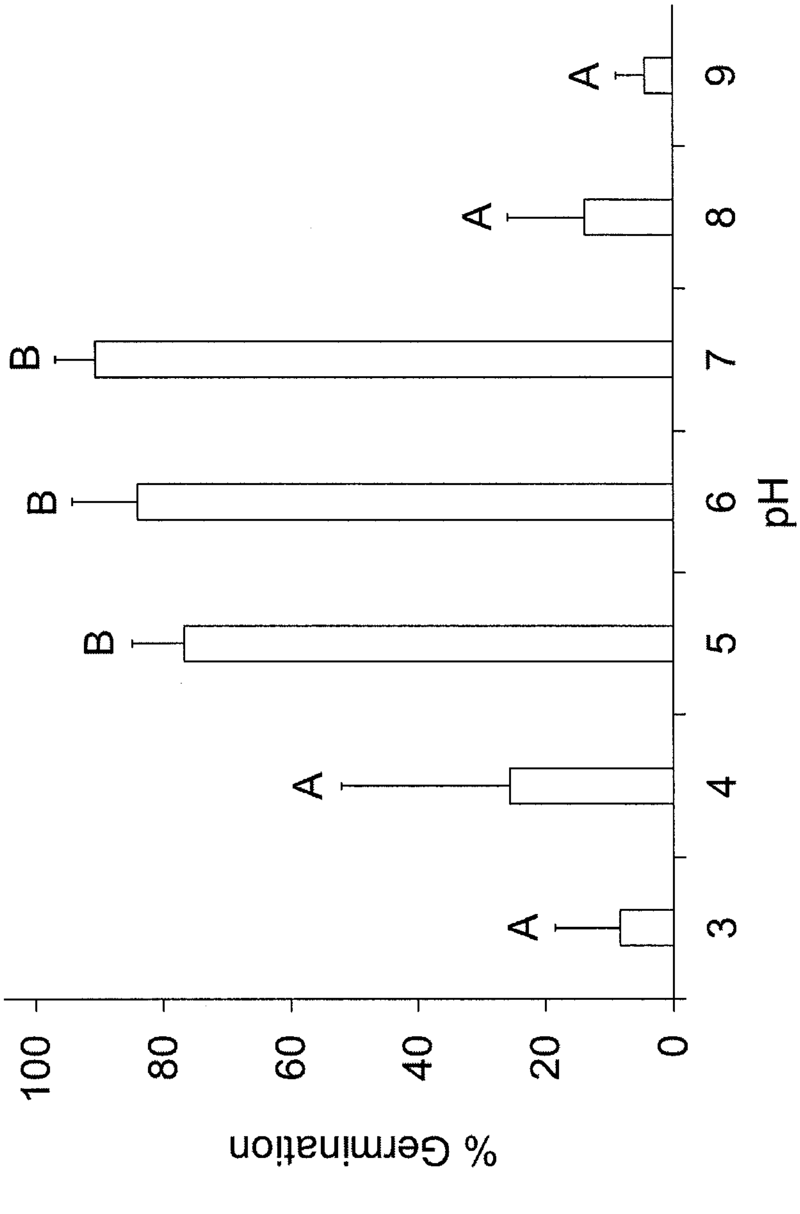

To determine the effects of temperature on *P. larvae* spore germination, a range of 25° C. to 42° C. was tested (FIG. 2A). At temperatures below 30° C., germination of *P. larvae* spores was slow. The maximal germination rates were observed at temperatures above 35° C. The ability of *P. larvae* spores to germinate also was tested at different pH levels (FIG. 2B). Spores failed to germinate in acidic or basic conditions; germination was optimal near neutral pH.

Titration of L-Tyrosine and Uric Acid for *P. larvae* Spore Germination

Figure 3A:
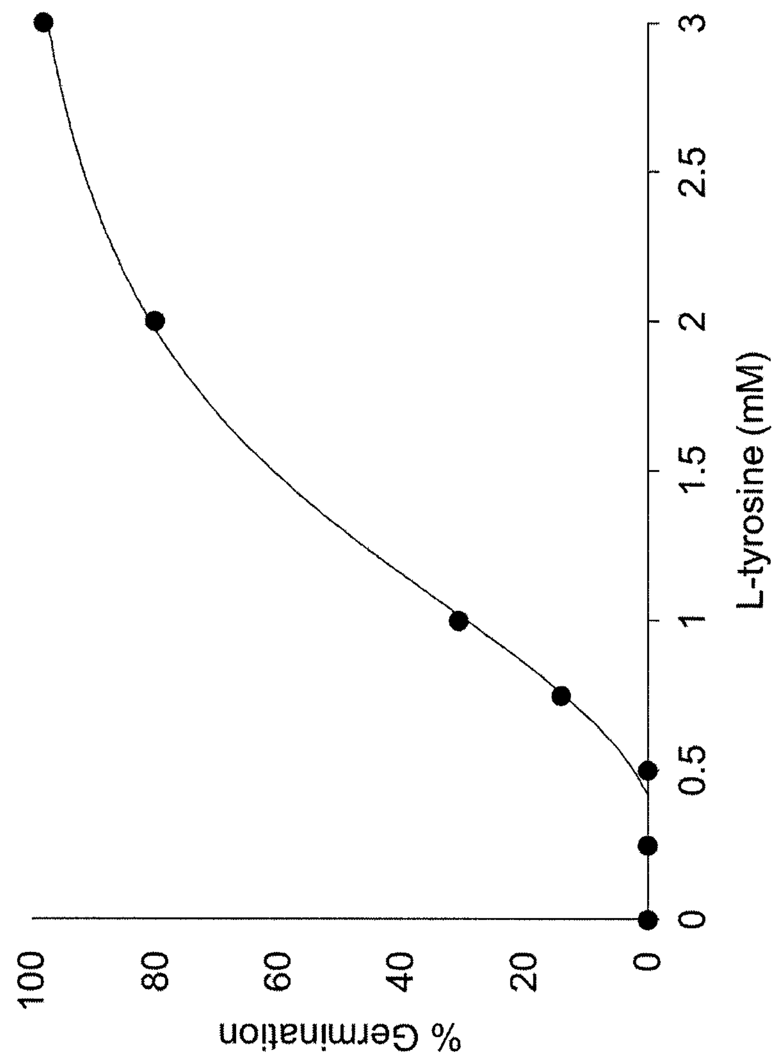
FIGS. 3A and 3B are graphs plotting dose response curves for *P. larvae* spores in various concentrations of L-tyrosine and uric acid.
Figure 3B:
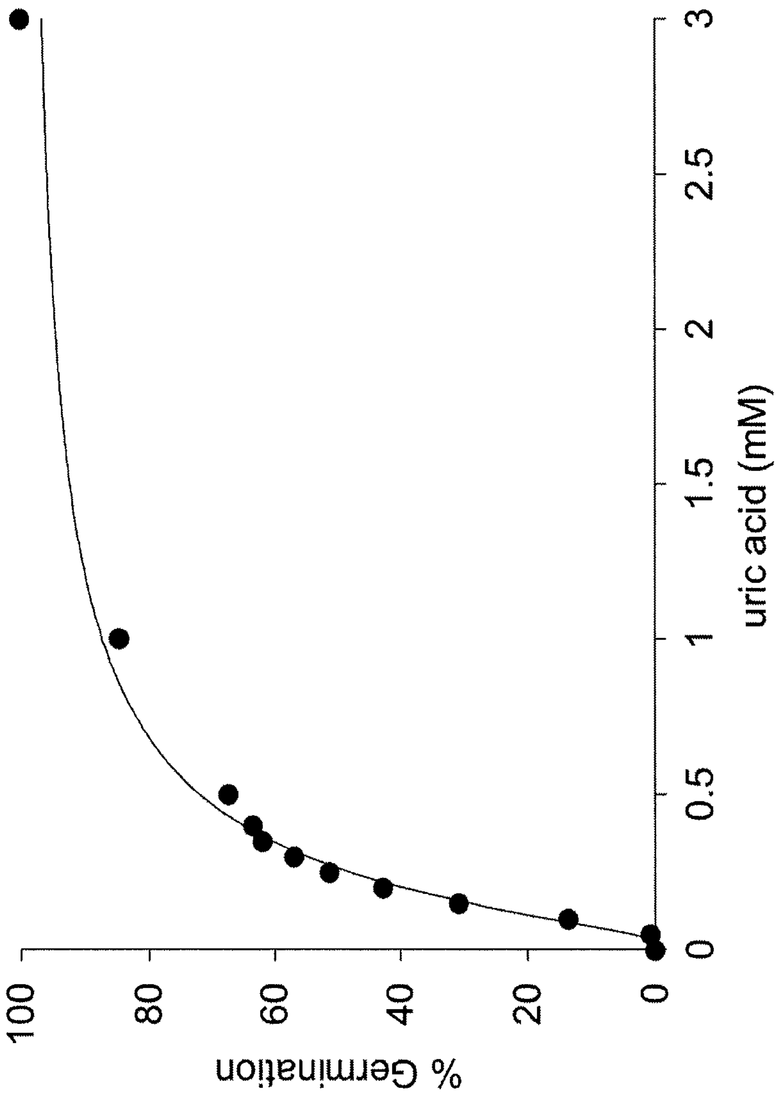

Titration of L-tyrosine at a saturating uric acid concentration yielded an $EC_{50}$ of 1.2 mM for L-tyrosine activation of *P. larvae* spore germination (FIG. 3A). Titration of uric acid at a saturating L-tyrosine concentration yielded an $EC_{50}$ of 0.2 mM for uric acid activation of *P. larvae* spore germination (FIG. 3B). Both dose response assays resulted in sigmoidal curves that passed the Durbin-Watson statistical test for autocorrelation.

Effects of L-Tyrosine and Purine Analogs on *P. larvae* Spore Germination

Since uric acid is a degradation product of purine catabolism, the ability of purine analogs to act as co-germinants of *P. larvae* spores was tested. As L-tyrosine is the only amino acid able to trigger *P. larvae* spore germination, its stereoisomer (D-tyrosine) and its side chain (phenol) also were tested as co-germinants with uric acid. In these experiments, however, none of the compounds tested was able to activate *P. larvae* spore germination.

Figure 4A:
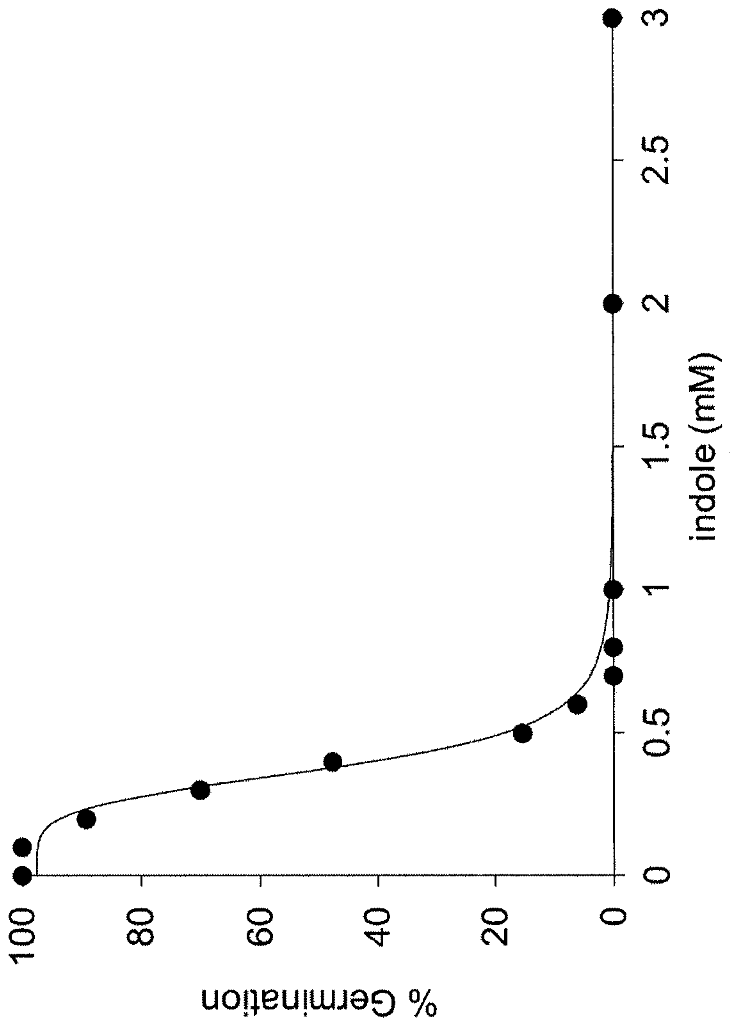
FIGS. 4A and 4B are graphs plotting dose response curves for *P. larvae* spores germinated with L-tyrosine/uric acid in the presence of various concentrations of indole or phenol.
Figure 4B:
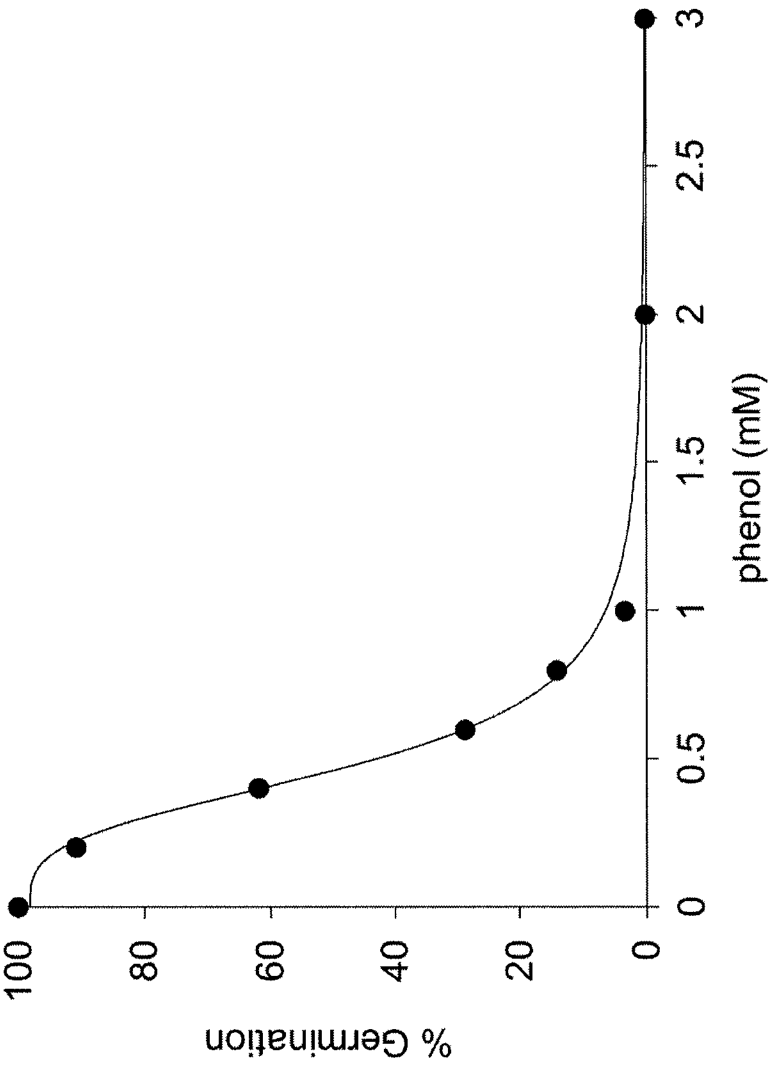

L-tyrosine and purine analogs were also tested for their ability to inhibit *P. larvae* germination. None of the purine analogs tested inhibited uric acid/L-tyrosine-induced germination of *P. larvae* spores. Similarly, D-tyrosine did not inhibit *P. larvae* spore germination. In contrast, indole (the side chain of tryptophan) and phenol (the side chain of tyrosine) both were able to inhibit *P. larvae* spore germination. Titrations of indole and phenol yielded an $IC_{50}$ of 0.37 mM for indole (FIG. 4A) and 0.46 mM for phenol (FIG. 4B) inhibition of *P. larvae* spore germination. Experiments using indole derivatives showed that 3-methylindole, 5-methylindole, and 7-methylindole retained inhibitory properties, with $IC_{50}$ values of 0.38, 0.37, and 0.28 mM, respectively (TABLE 1). In contrast, 1-N-methylindole neither activated nor inhibited *P. larvae* spore germination (TABLE 1). All dose response assays resulted in sigmoidal curves that passed the Durbin-Watson statistical test for autocorrelation.

To test the generality of *P. larvae* spore response, spores were prepared from *P. larvae* subsp. *pulvifaciens* strain ATCC 49843, and also from an environmental AFB sample. Based on phenotypic characteristics, the environmental sample was identified as *P. larvae* subsp. *larvae* (Genersch et al., *Appl. Environ. Microbiol.,* 71:7551-7555, 2005; and Genersch et al., *Int. J. Syst. Evol. Microbiol.,* 56:501-511, 2006). Spores of both *P. larvae* sub-species responded identically to L-tyrosine and uric acid, and their germination was similarly inhibited by indole and phenol.

TABLE 1

Effect of indole methylation on *P. larvae* spore germination

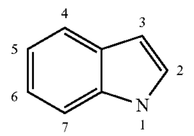

| Compound | $IC_{50}$ (mM) |
|---|---|
| Indole | 0.33 |
| Phenol | 0.46 |
| 1-N-methylindole | N/A |
| 3-methylindole | 0.38 (0.01) |
| 5-methylindole | 0.37 (0.02) |
| 7-methylindole | 0.28 (0.01) |

*P. larvae* spores were incubated with various concentrations of indole analogs for 15 minutes prior to addition of 3 mM urea and 3 mM L-tyrosine. $IC_{50}$ was calculated by plotting percent germination vs. indole analog concentration. Standard deviations are shown in parentheses. N/A, No activity under the conditions tested.

Example 2

Inhibitory Effect of Indole Analogs Against *P. larvae* in Honeybee Larvae

Materials and Methods

Materials:

Chemicals were from the Sigma-Aldrich Corporation (St. Louis, Mo.) and VWR International (Radnor, Pa.). The dehydrated culture medium was obtained from BD Difco (Franklin Lakes, N.J.). *Paenibacillus larvae* subsp. *pulvifaciens* strain ATCC 49843 was from the American Tissue Culture Collection (ATCC). Lyophilized royal jelly from GloryBee Foods (Eugene, Oreg.) was stored at −20° C. until used for diet preparation.

*P. larvae* Spore Preparation:

*P. larvae* strains were grown on BD tryptic soy agar plates for 7 days in a 5% $CO_2$ incubator at 37° C. The resulting bacterial lawns were collected by flooding with ice-cold deionized water. Spores were pelleted by centrifugation and resuspended in fresh deionized water. After three washing steps, the spores were separated from their vegetative and partially sporulated forms by centrifugation through a 20%-to-50% HistoDenz gradient. The spore pellet was washed five times with water and stored at 4° C. Spore preparations were 90% pure as determined by microscopic observation of Schaeffer-Fulton-stained samples.

Antagonists of *P. larvae* Spore Germination:

To test for possible antagonists of *P. larvae* spore germination, spores were individually supplemented with 0.4 mM indole analog or 0.4 mM phenol analog. Spore suspensions were incubated for 15 minutes at room temperature while monitoring the $OD_{580}$. If no germination was detected, L-tyrosine and uric acid were added to final concentrations of 3 mM, and germination was monitored as described above. Germination rates for other conditions were divided by the uninhibited maximum germination rate obtained with 3 mM L-tyrosine-3 mM uric acid and are reported as percent germination.

Inhibition of *P. larvae* Spore Germination by Indole and Phenol:

*P. larvae* spores were individually incubated with various concentrations of indole, phenol, 1-N-methylindole, 3-methylindole, 5-methylindole, or 7-methylindole. After a 15 minute incubation, the spores were treated with 3 mM L-tyrosine-3 mM uric acid. The germination rate was set to 100% for *P. larvae* spores germinated in the absence of inhibitor. Germination rates for other conditions were divided by the uninhibited maximum germination rate obtained with 3 mM L-tyrosine-3 mM uric acid, and are reported as percent germination. Percent germination was plotted against the inhibitor concentrations. The resulting sigmoidal curves were fitted using the four-parameter logistic function in SigmaPlot v.9 to calculate the germination 50% inhibitory concentrations ($IC_{50}$).

Acquisition of $1^{st}$ Instar *Larvae:*

First instar honey bee larvae were obtained from two colonies headed by naturally mated queens (Honey Bee Genetics, Vacaville Calif.). Queens were trapped on empty frames within a cage constructed with queen excluder. Worker bees can fit through the excluder but the queen cannot exit the cage. The frame was placed within the brood chamber to stimulate egg laying by the queen overnight. Eggs were incubated in the hive for 4 days to allow newly hatched larvae to be fed by nurse bees. First instar honey bee larvae were brought into the laboratory and stored in a 35° C. 85% relative humidity chamber before grafting.

Sterile six well plates with a well volume of 17.0 ml were filled with 2.5 ml of pre-warmed artificial worker jelly. Honey bee larvae were transferred into each well using the thin tongue made of flexible plastic from a Chinese grafting tool. The plastic grafting tool was decontaminated with 70% ethanol throughout usage. Grafting was performed in the sterile environment of a honey bee laboratory, and honey bee larvae were then transferred to a bacterial spore laboratory for control and spore exposure treatments.

Artificial Worker Jelly Preparation:

Artificial worker jelly was prepared using a lyophilized royal jelly, D-glucose, D-fructose, yeast extract, and autoclaved double distilled water. Ingredients minus lyophilized royal jelly were dissolved in autoclaved double distilled water. Lyophilized royal jelly was added to this sugar-yeast extract solution and mixed thoroughly with a vortex mixer. Artificial diet was prepared an hour prior to use for larval rearing. To reduce the development of worker-queen hybrids because of nutrition, the composition and amounts of artificial worker jelly were controlled in every larval stage.

Incubation Conditions:

Honey bee larvae were incubated in an air tight plastic container placed inside an incubator. The desired relative humidity (95%) and temperature (35° C.) was verified with an iButton data logger (Maxim Integrated; San Jose, Calif.). The appropriate relative humidity was obtained by placing a solution of 20% glycerol by weight. The plastic containers were was decontaminated throughout usage with detergent, 70% ethanol, and treated with an ultraviolet lamp overnight.

Rearing Procedure:

Feeding of diets was performed daily in different amounts according to Table 2. The amount of diet consumed by larvae was assumed based on published literature. A micropipette was used to place a food drop next to the mouth of the larvae. Drowning was avoided by maintaining the appropriate humidity and water content of diet. Forty first and second instar larvae were placed into one well of a six well plate. Third instar larvae were transferred individually to 48 well plates filled with fresh food.

Larval survival was determined daily by observing signs of respiration, disease symptoms, and other abnormalities with a stereo microscope. The number of dead larvae was recorded, and surviving larvae were fed fresh food. The start of pupation was indicated by the appearance of uric acid crystals and light yellow excretions in the remaining food. Any larvae that failed to pupate were considered to have died on day seven.

Indole Analog Application:

The concentration of indole analogs applied to the larval diet was selected based on preliminary experiments with indole. When 0.5 mM indole was incorporated into the larval diet, larvae were protected from development of AFB disease. Each indole analog was dissolved in warm autoclaved water to provide a stock solution that could be used to produce artificial worker jelly. Artificial worker jelly containing indole analogs was not frozen, because the solubility of solutes is dependent on temperature.

Survival Analysis:

The larval survival data was analyzed using the LogRank test in SigmaPlot. The LogRank test determines if there are significant differences between survival curves and then identifies pairs of curves that are significantly different.

Results

Figure 5:
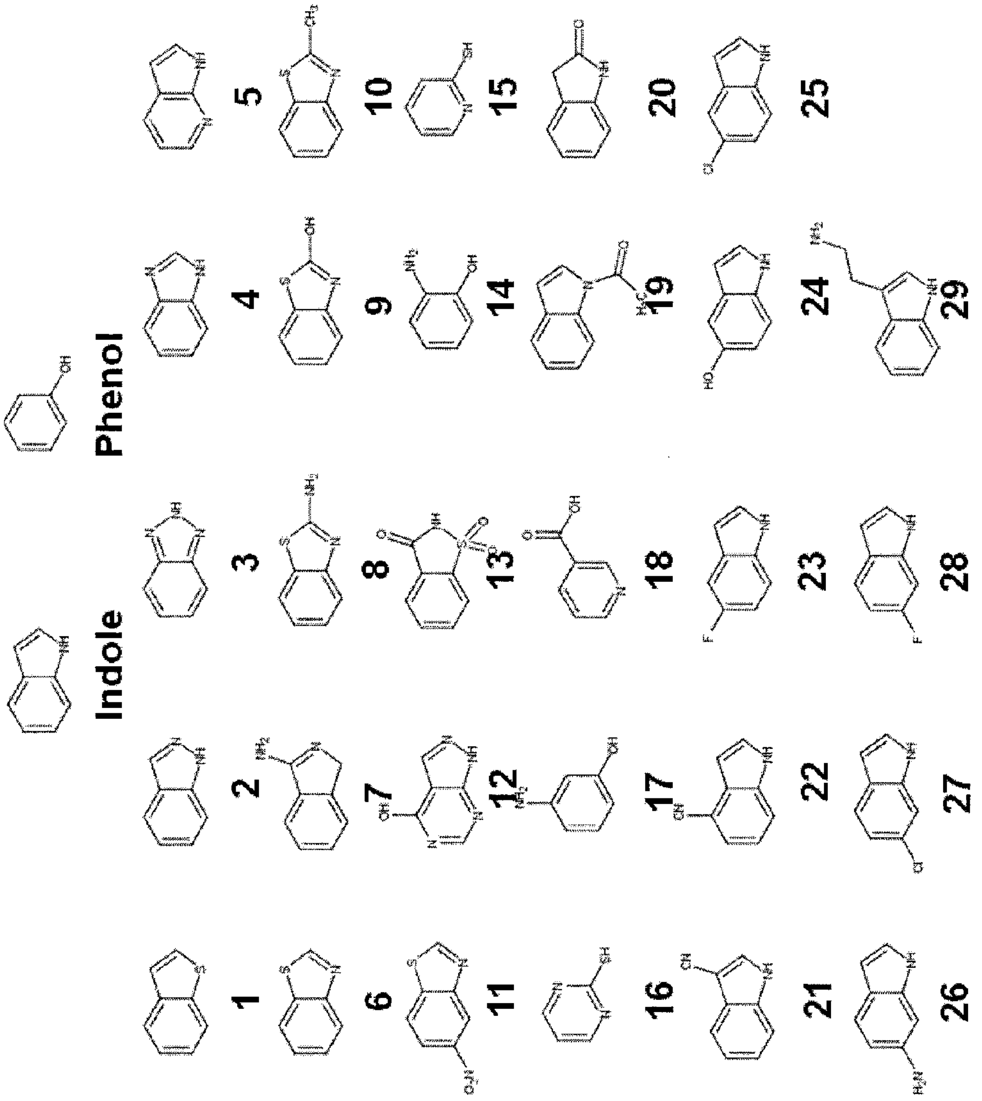
FIG. 5 is a diagram showing compounds tested as antagonists of *P. larvae* spore germination in Example 2 herein. 1. Thionaphthene; 2. Indazole; 3. 1H-Benzotriazole; 4. Benzimidazole; 5. 7-Azaindole; 6. Benzothiazole; 7. 1H-Isoindol-3amine; 8. 2-Aminobenzothiazole 9. 2-Hydroxybenzothiazole; 10. 2-Methylbenzothiazole; 11.

Indole ($IC_{50}$ 0.4 mM) and phenol ($IC_{50}$ 0.5 mM) were previously shown to inhibit *P. larvae* spore germination. To identify functional groups that enhance inhibitor binding to germination receptor, and potentially identify stronger inhibitors, the effect of 33 indole and phenol structural analogues on *P. larvae* spore germination was tested in vitro (FIG. 5). The compounds were tested at 0.4 mM.

The screen included indole structural analogues that consisted of a six-membered benzene ring fused to a five-membered ring. Substitution of the nitrogen at position 1 of indole with a sulfur group failed to significantly change *P. larvae* spore germination. The addition of nitrogen to position 2, 2+3, 3, or 7 also did not significantly affect spore germination. Further, addition of functional groups to the above-mentioned analogues did not significantly alter *P. larvae* spore germination. Similar effects were observed with the phenol structural analogues tested.

*P. larvae* spore germination was, however, significantly affected by indole analogs with electron withdrawing groups. Titration of these indole analogues at saturating uric acid/L-tyrosine concentrations were performed to obtain $IC_{50}$ values (TABLE 2). The maximum effect on *P. larvae* spore germination was observed on indole with halides groups. The dose response assays resulted in sigmoidal curves, which passed the Durbin-Watson statistical test for autocorrelation.

5-Chloroindole was then tested in vitro, using *P. larvae* cells or spores. The inhibitory effect of 5-chloroindole on *P. larvae* cells is shown in FIGS. 6A-6D. *P. larvae* cells were grown in medium containing different concentrations of DMSO, complex medium (MYPGP), or 0.5 to 2 mM 5-chloroindole, and cellular growth was monitored over a 24 hour period. 1, 1.5 and 2 mM 5-chloroindole significantly inhibited *P. larvae* growth at all time points as compared to medium control (Analysis of Variance, Log-rank test, $p<0.05$).

The inhibitory effect of 5-chloroindole on *P. larvae* spores is shown in FIGS. 7A-7D. *P. larvae* spores were grown in medium containing different concentrations of DMSO, complex medium (MYPGP), or 0.5 to 2 mM 5-chloroindole, and cellular growth was monitored over a 24 hour period. 5-chloroindole had no significant effect as compared to medium control at 6 hours (FIG. 7A), and at 12 hours the growth with all concentrations of 5-chloroindole and DMSO were significantly different than medium control (FIG. 7B). At 18 and 24 hours, however, all concentrations of 5-chloroindole significantly inhibited *P. larvae* growth, as compared to medium control (Analysis of Variance, Log-rank test, $p<0.05$), while DMSO alone was not significantly different.

TABLE 2

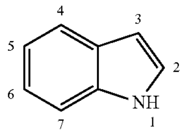

| Indole Analog | $IC_{50}$ (mM) |
|---|---|
| Indole | 0.37 ± .02 |
| 4-cyanoindole | 0.20 ± .02 |
| 5-bromindole | 0.06 ± .07 |
| 5-chloroindole | 0.03 ± .01 |
| 5-fluoroindole | 0.12 ± .02 |
| 5-hydroxyindole | 0.55 ± .17 |
| 5-nitroindole | 0.07 ± .01 |
| 6-bromoindole | 0.06 ± .06 |
| 6-chloroindole | 0.02 ± .00 |
| 6-cyanoindole | 0.11 ± .01 |
| 6-fluoroindole | 0.12 ± .01 |

The effectiveness of various halo indole compounds were then tested in vivo by assessing their effects on survival of honey bee larvae contacted with *P. larvae* spores. For example, FIG. 8A shows survival curves for honey bee larvae fed larval diet (wj) supplemented with 0.5 mM of 5-bromoindole, 5-chloroindole, 5-nitroindole, 6-bromoindole, or 6-chloroindole, while FIG. 8B shows survival curves for honey bee larvae fed larval diet (wj) supplemented with the same indole analogues and *P. larvae* spores. Differences between survival curves were determined using Kaplan-Meier analysis and Log-Rank test ($p<0.002$). All of the analogs increased survival as compared to treatment with *P. larvae* spores alone, with 5-bromoindole and 5-chloroindole having the greatest effect (FIG. 8B).

The effect of 5-chloroindole was further studied by testing various concentrations of the compound. As shown in FIG. 9A, the survival of honey bee larvae fed larval diet (wj) supplemented with 0.75 or 1 mM 5-chloroindole at 7 days was similar to the survival of honey bee larvae fed wj alone. FIG. 9B shows survival curves of honey bee larvae fed larval diet (wj) supplemented with *P. larvae* spores and concentrations of 5-chloroindole ranging from 0.125 mM to 1 mM. In general, the ability of 5-chloroindole to increase survival was directly correlated to its concentration. Differences between survival curves were determined using Kaplan-Meier analysis and Log-Rank test ($p<0.001$).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for preventing germination of a *Paenibacillus larvae* spore, comprising contacting said spore with a compound of Formula (I):

(I)

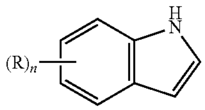

or a pharmaceutically acceptable salt thereof, wherein:

each R is independently selected from unsubstituted ($C_1$-$C_6$)alkyl; unsubstituted ($C_2$-$C_6$)alkenyl; unsubstituted ($C_2$-$C_6$)alkynyl; halo; ($C_1$-$C_6$)haloalkyl; CN; and $NO_2$; and n is an integer from 0 to 2;

wherein said spore is contacted with said compound in an amount effective to prevent germination of said spore.

2. The method of claim 1, wherein n is 1.

3. The method of claim 2, wherein R is halo.

4. The method of claim 1, wherein R is unsubstituted ($C_1$-$C_6$)alkyl.

5. The method of claim 1, wherein R is $CH_3$.

6. The method of claim 1, wherein the compound of Formula (I) is selected from:

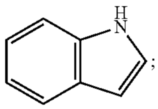
;
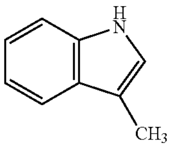
;
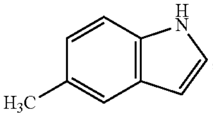
; and
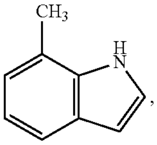
, or a pharmaceutically acceptable salt thereof.

7. The method of claim 1, wherein the compound is selected from 4-cyanoindole, 5-bromindole, 5-chloroindole, 5-fluoroindole, 5-hydroxyindole, 5-nitroindole, 6-bromoindole, 6-chloroindole, 6-cyanoindole, and 6-fluoroindole.

8. The method of claim 1, wherein n is 2.

9. The method of claim 1, wherein R is unsubstituted ($C_1$-$C_6$)alkyl, unsubstituted ($C_2$-$C_6$)alkenyl, unsubstituted ($C_2$-$C_6$)alkynyl, or unsubstituted ($C_1$-$C_6$)haloalkyl.

10. The method of claim 1, wherein R is halo, CN, or $NO_2$.

11. The method of claim 1, wherein n is 1, and wherein R is unsubstituted ($C_1$-$C_6$)alkyl, unsubstituted ($C_2$-$C_6$)alkenyl, unsubstituted ($C_2$-$C_6$)alkynyl, or unsubstituted ($C_1$-$C_6$)haloalkyl.

12. The method of claim 1, wherein n is 2, and wherein R is unsubstituted ($C_1$-$C_6$)alkyl, unsubstituted ($C_2$-$C_6$)alkenyl, unsubstituted ($C_2$-$C_6$)alkynyl, or unsubstituted ($C_1$-$C_6$) haloalkyl.

13. The method of claim 1, wherein n is 1, and wherein R is halo, CN, or $NO_2$.

14. The method of claim 1, wherein n is 2, and wherein R is halo, CN, or $NO_2$.

15. The method of claim 1, wherein the compound of Formula (I) is selected from:

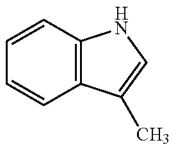
;
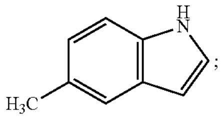
; and
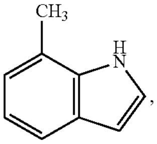
, or a pharmaceutically acceptable salt thereof.

16. A method for preventing germination of a *Paenibacillus larvae* spore, comprising contacting said spore with a compound selected from 4-cyanoindole, 5-bromindole, 5-chloroindole, 5-fluoroindole, 5-hydroxyindole, 5-nitroindole, 6-bromoindole, 6-chloroindole, 6-cyanoindole, and 6-fluoroindole, wherein said spore is contacted with said compound in an amount effective to prevent germination of said spore.

* * * * *